United States Patent
Purcell et al.

(10) Patent No.: US 8,657,832 B2
(45) Date of Patent: Feb. 25, 2014

(54) METHOD AND DEVICE FOR IMPLANT DEPLOYMENT

(75) Inventors: Thomas Purcell, Del Mar, CA (US); William Reimels, Oceanside, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 848 days.

(21) Appl. No.: 12/456,602

(22) Filed: Jun. 18, 2009

(65) Prior Publication Data

US 2009/0318928 A1 Dec. 24, 2009

Related U.S. Application Data

(60) Provisional application No. 61/132,499, filed on Jun. 18, 2008.

(51) Int. Cl.
*A61B 17/88* (2006.01)

(52) U.S. Cl.
USPC .......................................................... 606/99

(58) Field of Classification Search
USPC .................. 606/99, 86 A, 104; 623/17.11
See application file for complete search history.

(56) References Cited

U.S. PATENT DOCUMENTS

| | | | | |
|---|---|---|---|---|
| 5,800,549 | A * | 9/1998 | Bao et al. ........................ | 606/99 |
| 6,319,257 | B1 * | 11/2001 | Carignan et al. ................ | 606/99 |
| 6,471,709 | B1 * | 10/2002 | Fawzi et al. .................... | 606/114 |
| 7,081,123 | B2 * | 7/2006 | Merboth et al. ............... | 606/185 |
| 7,278,972 | B2 * | 10/2007 | Lamoureux et al. ........... | 600/567 |
| 7,338,456 | B2 * | 3/2008 | Goldenberg ................... | 600/564 |
| 7,384,400 | B2 * | 6/2008 | Goldenberg ................... | 600/564 |
| 2002/0026197 | A1 | 2/2002 | Foley | |

* cited by examiner

*Primary Examiner* — Michael T Schaper
*Assistant Examiner* — Michael Araj
(74) *Attorney, Agent, or Firm* — Michael J. Loi

(57) ABSTRACT

A surgical implant insertion system for deployment and removal of an implant into a vertebral body. The system includes an actuation rod, an actuator handle coupled to the actuation rod, and an inserter locking tube disposed over the actuation rod and coupled to an inserter handle. Upon insertion of the implant into the vertebral body using the inserter handle, the actuator handle is turned causing the actuation rod to expand or compress the implant disposed at a distal end of the inserter locking tube.

11 Claims, 32 Drawing Sheets

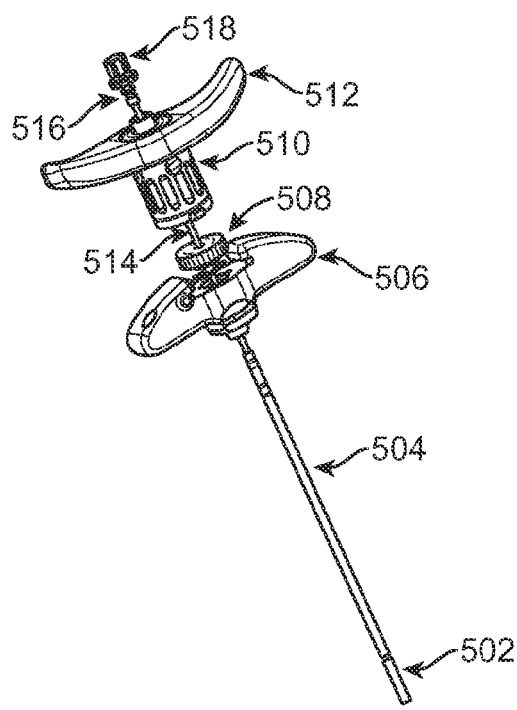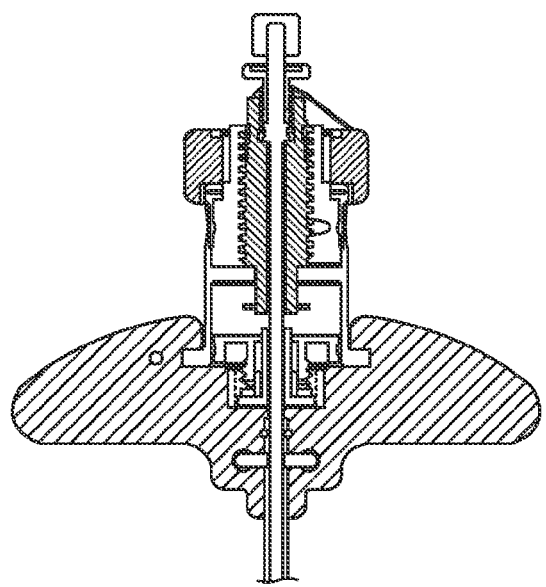
FIG. 5A                FIG. 5B
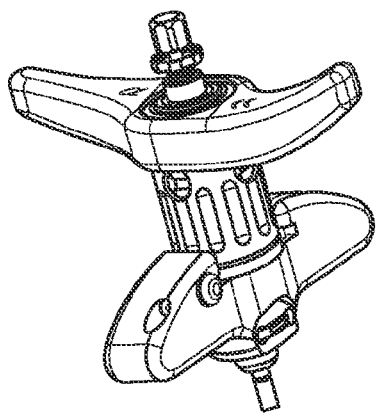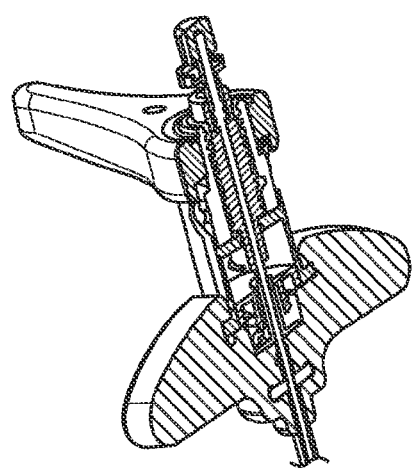
FIG. 5C                FIG. 5D

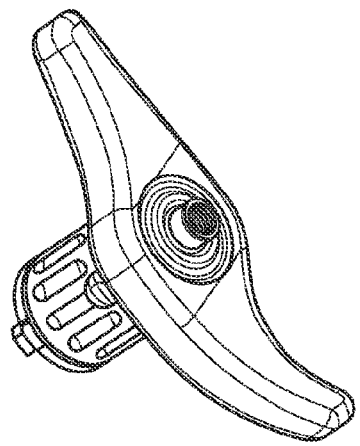
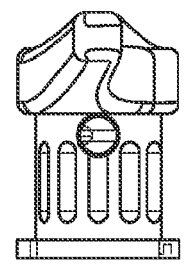
FIG. 6A　　　　　　FIG. 6B
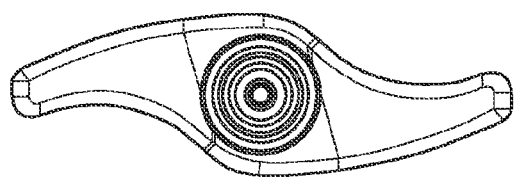
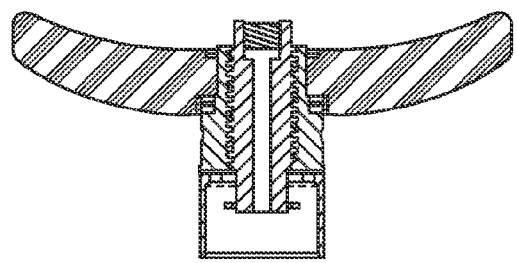
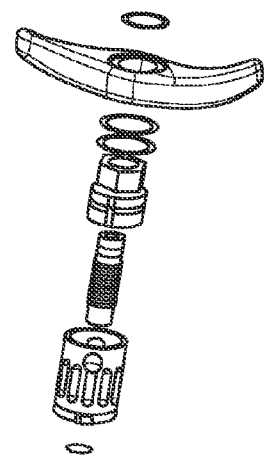
FIG. 6C　　　　　　FIG. 6D Actual undeployed implant    Actual deployed implant 4.5mm undeployed model    4.5mm deployed model 5.5mm undeployed model    5.5mm deployed model 7.0mm undeployed model    7.0mm deployed model

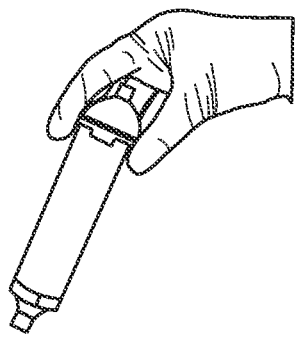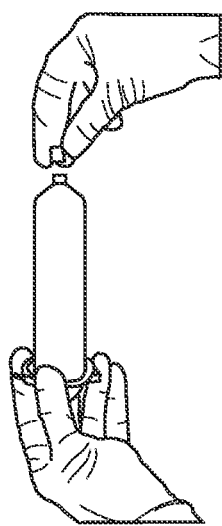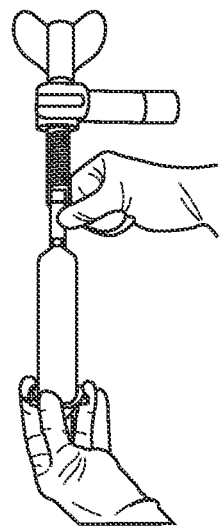
FIG. 17X  FIG. 17Y  FIG. 17Z
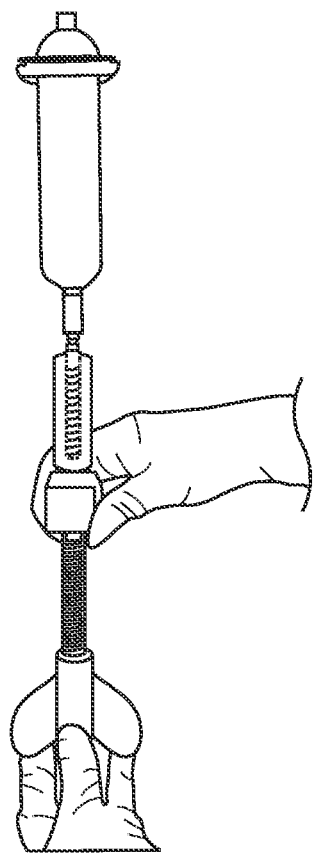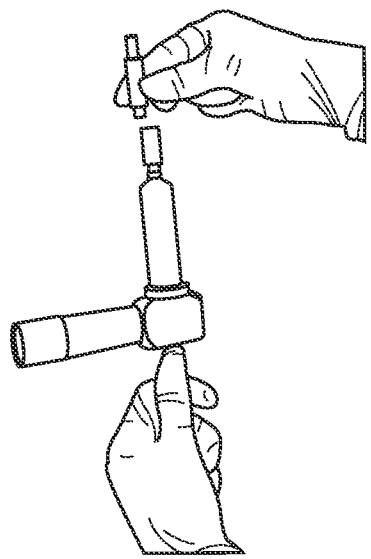
FIG. 17BB
FIG. 17AA

METHOD AND DEVICE FOR IMPLANT DEPLOYMENT

CROSS-REFERENCES TO RELATED APPLICATIONS

The present application claims priority to U.S. Provisional Patent Application No. 61/132,499 to Purcell, filed Jun. 18, 2008, and entitled "METHOD AND DEVICE FOR IMPLANT DEPLOYMENT", the disclosure of which is incorporated herein by reference in its entirety.

BACKGROUND OF THE INVENTION

1. Field of the Invention

The present invention generally relates to the field of spinal surgery. In particular, the present invention relates to the field of surgical access to the spine. More particularly, the present invention relates to systems and methods of deployment of an implant, e.g., a stent.

2. Background

The spine is a series of individual bones called vertebrae, separated by cartilaginous disks. The spine includes seven cervical (neck) vertebrae, 12 thoracic (chest) vertebrae, five lumbar (lower back) vertebrae, and the fused vertebrae in the sacrum and coccyx that help to form the hip region. While the shapes of individual vertebrae differ among these regions, each is essentially a short hollow tube containing the bundle of nerves known as the spinal cord. Individual nerves, such as those carrying messages to the arms or legs, enter and exit the spinal cord through gaps between vertebrae. The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. The spine curves in at the lumbar region, back out at the thoracic region, and back in at the cervical region.

SUMMARY OF THE INVENTION

In some embodiments, the present invention relates to an surgical implant insertion system for deployment and removal of an implant into a vertebral body. The system includes an actuation rod, an actuator handle coupled to the actuation rod, and an inserter locking tube disposed over the actuation rod and coupled to an inserter handle. Upon insertion of the implant into the vertebral body using the inserter handle, the actuator handle is turned causing the actuation rod to expand or compress the implant disposed at a distal end of the inserter locking tube.

BRIEF DESCRIPTION OF THE DRAWINGS

The present invention is described with reference to the accompanying drawings. In the drawings, like reference numbers indicate identical or functionally similar elements.

FIGS. 5A-5I are detailed views of an exemplary system for deployment of an implant, according to some embodiments of the present invention.

FIGS. 6A-D are various views of an exemplary actuator component of the system for deployment of an implant, according to some embodiments of the present invention.

DETAILED DESCRIPTION OF THE INVENTION

FIGS. 1A-16 illustrate exemplary embodiments of the systems and methods for deploying an implant, such as a stent. Examples of stents are shown in FIG. 13 (in undeployed/unexpanded and deployed/expanded states) disclosed in U.S. Pat. No. 5,807,275 assigned to Stout Medical Group. The stents have initial (pre-deployment) diameters in a range of approximately 4.5 mm to approximately 7.0 and initial lengths of approximately 1.04 mm to approximately 1.34 mm. When stents are deployed into a body of a patient, the stents can be expanded. In some embodiments, the diameters of deployed stents can be in a range of approximately 11.4 mm to approximately 14.8 mm, whereas their length can be in a range of approximately 22.8 mm to approximately 31.7 mm. As can be understood by one skilled in the art, other diameters and lengths of stents are possible. Further, the present invention can be configured to deliver any types of implants.

An exemplary system for deployment of implants is illustrated in connection with FIGS. 1A-12B, 15-16 and 19A-19W. Exemplary methods for deployment of implants is illustrated in FIGS. 14A-14DD, 17A-17FF and 18A-18C.

Figures 1A, 1B, 1C:
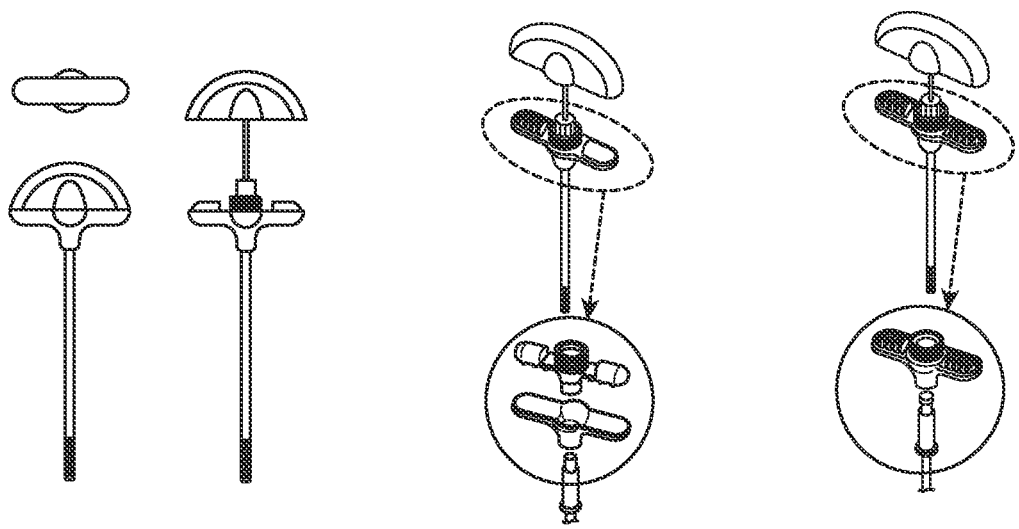
FIGS. 1A-K illustrate an exemplary system for deployment of an implant, according to some embodiments of the present invention.
Figures 1D, 1E:
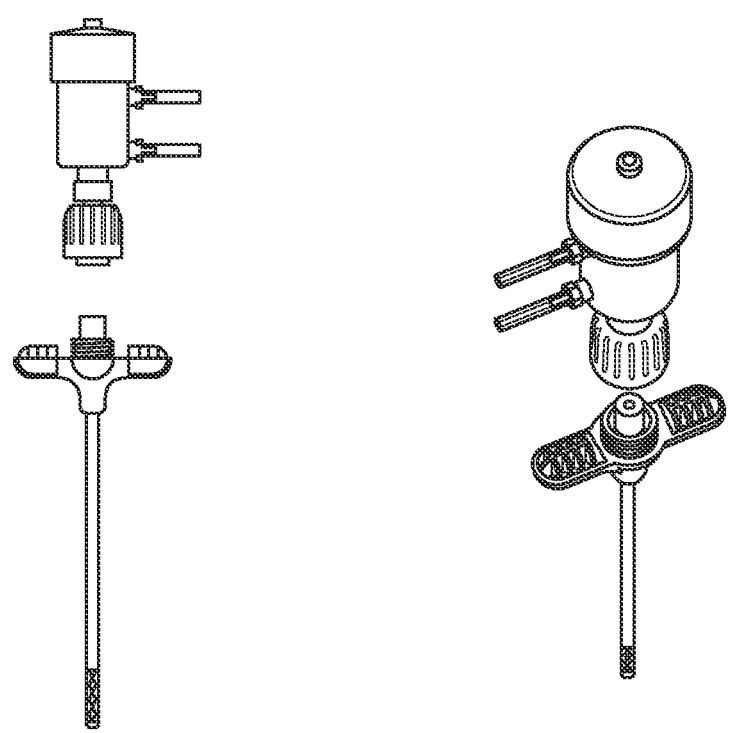
Figure 1F:
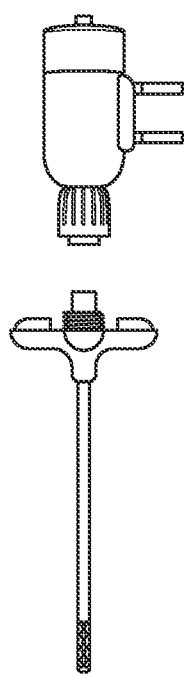
Figure 1G:
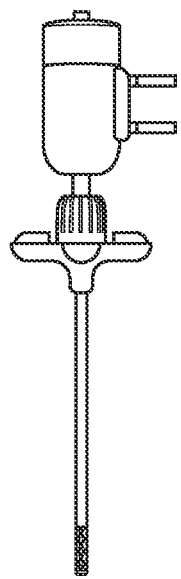
Figure 1H:
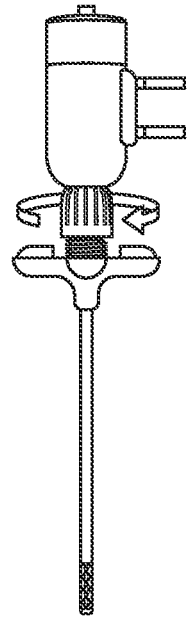
Figure 1I:
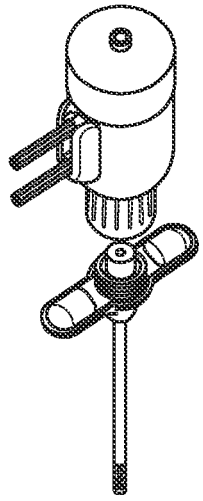
Figure 1J:
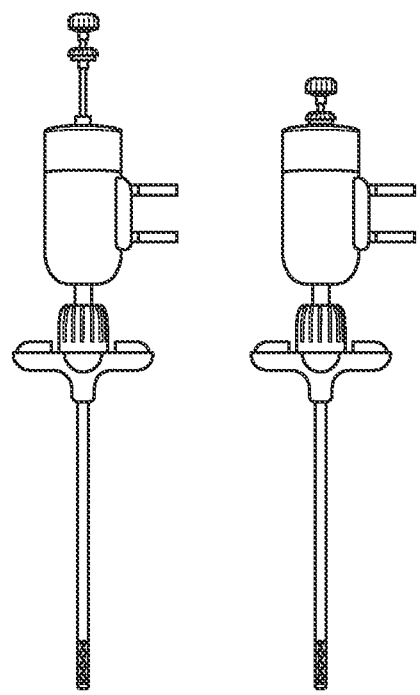
Figure 1K:
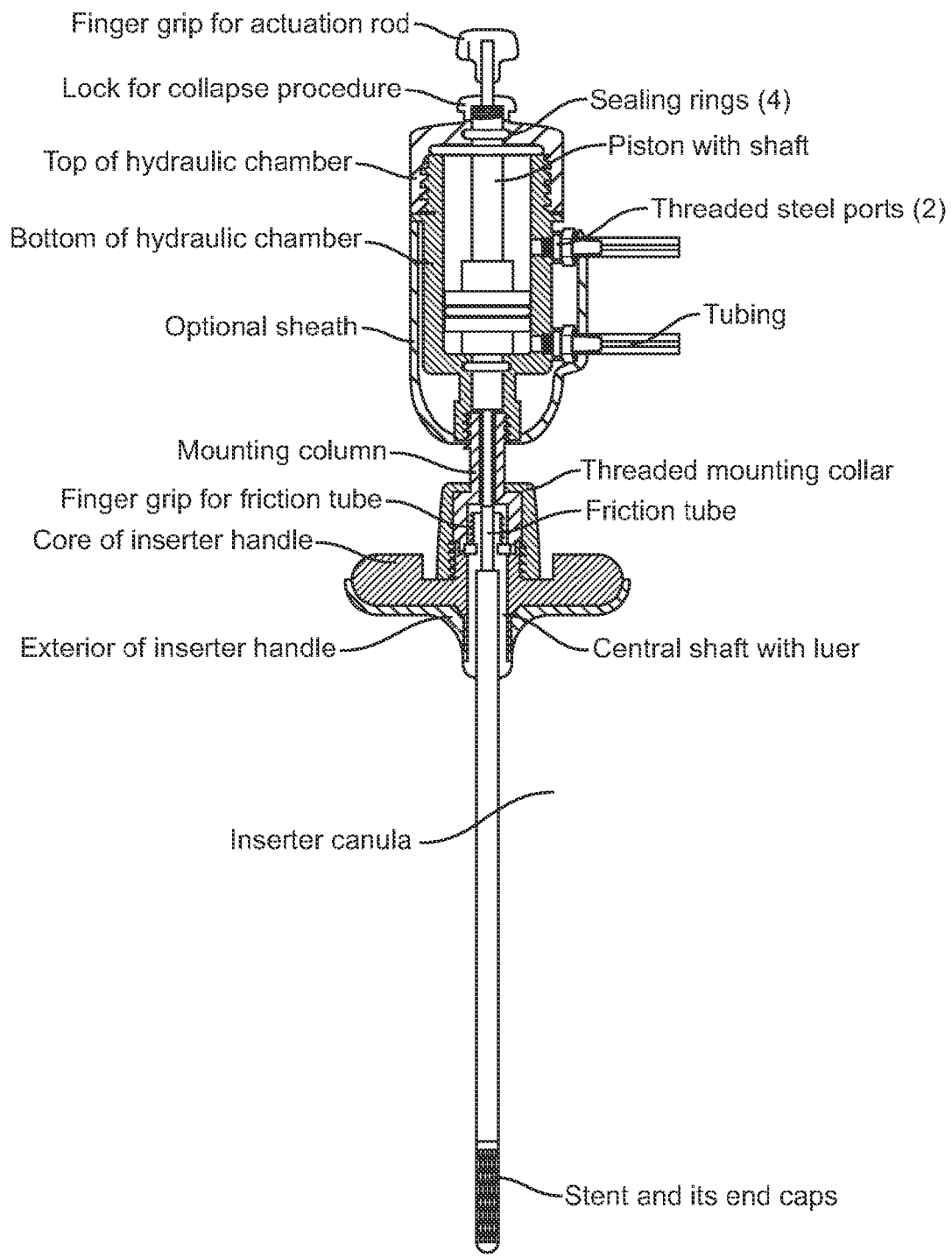

Referring to FIGS. 1A-1K, an exemplary implant inserter is illustrated, according to some embodiments of the present invention. FIG. 1K illustrates a hydraulic implant deploy/collapse device. The device includes an inserter cannula having a proximate end and a distal end. The distal end is coupled to the implant (e.g., a stent) and its end caps. The proximate end is coupled to the inserter handle. The inserter handle includes an exterior portion and a core. A central shaft with luer is configured to be contained within the handle and secures the inserter cannula within the handle. A threaded mounting collar is configured to be mounted to the inserter handle and can be threadedly secured to the handle using a threaded ring. The device further includes a friction tube disposed inside the cannula and the handle. The friction tube is allows for deployment and/or collapse of the implant upon actuation of a hydraulic mechanism coupled to the inserter handle via a mounting column. The mounting column is further coupled to a hydraulic chamber containing the hydraulic mechanism. The chamber includes a top portion and a bottom portion. The top portion includes a piston with a shaft configured to drive the deployment/collapse procedures. The chamber is further sealed at the top using a plurality of sealing rings (in some embodiments, there are four rings). The hydraulic chamber further includes a finger grip portion for actuation of a rod, where the finger grip portion is coupled to the top portion of the chamber. The top portion of the chamber also includes a locking mechanism for performing a collapse procedure of the implant. The bottom portion of the chamber includes tubing coupled to the chamber via a plurality of threaded steel ports. The chamber can also include an optional sheath.

Figure 14A:
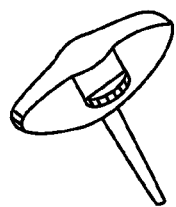
FIGS. 14A-Z and 14AA-EE illustrate an exemplary spinal reduction/correction method, according to some embodiments of the present invention.
Figure 14D:
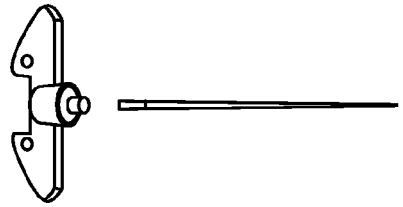
Figure 14B:
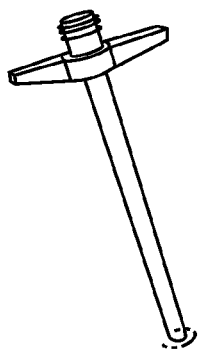
Figure 14E:
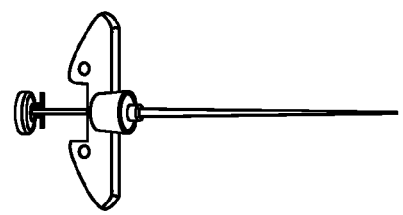
Figure 14C:
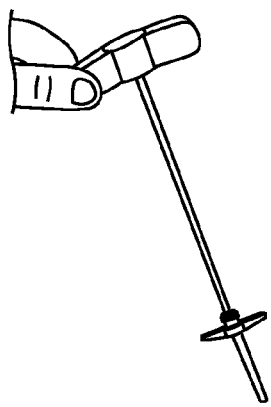
Figure 15:
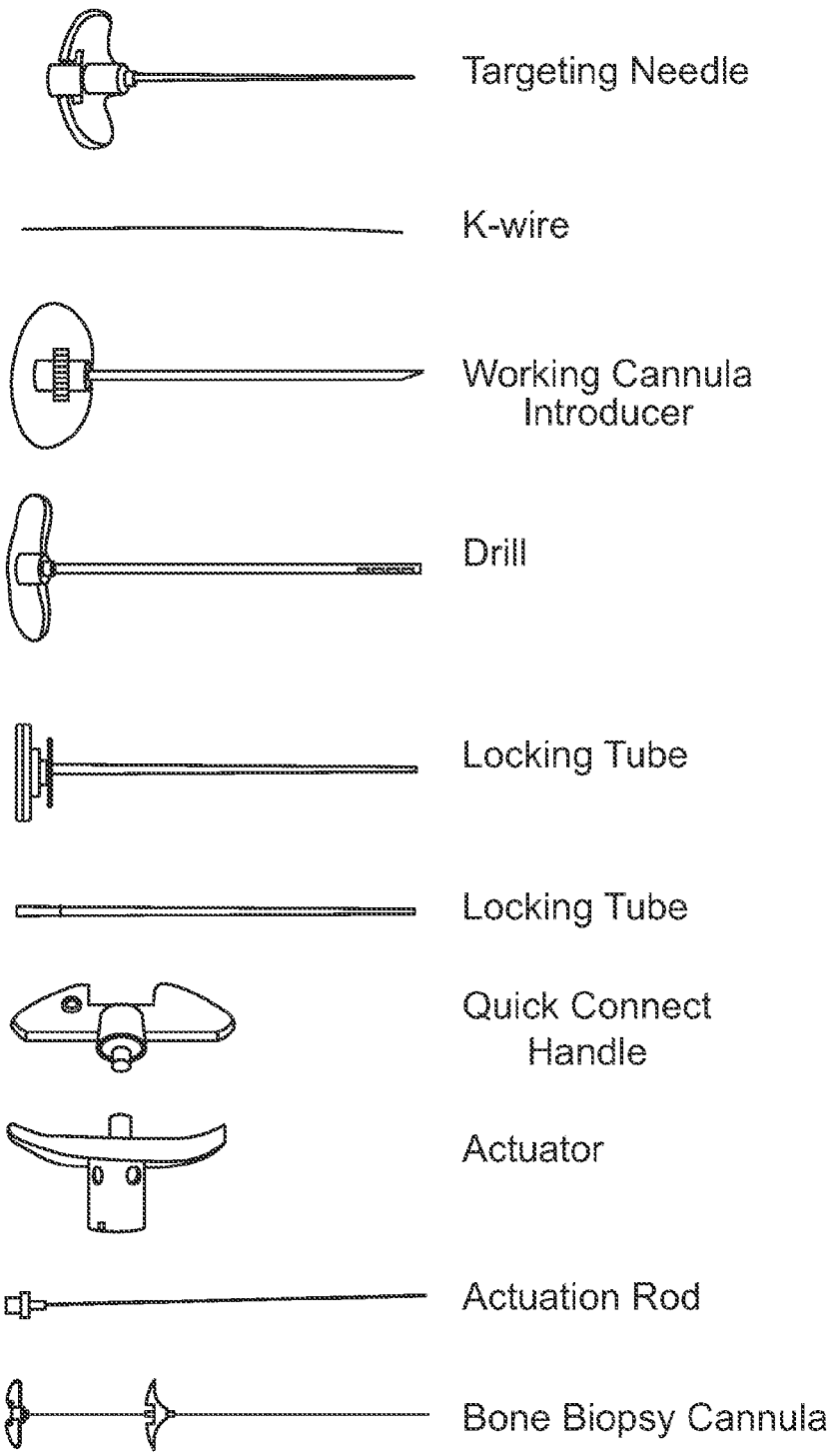
FIG. 15 illustrates various instruments involved in the system for deployment of an implant, according to some embodiments of the present invention.

FIG. 15 illustrates instruments used in connection with surgical deployment procedures shown in FIGS. 14A-14EE.

FIGS. 1A illustrate the implant inserter in an open and a closed state, respectively. The implant inserter includes a threaded ring that provides a mounting base for a hydraulic deploy/collapse mechanism. FIGS. 1B-1C illustrate the implant inserter in further detail. As illustrated in FIG. 1B, the implant inserter includes a central column with a luer lock that is joined to a single grip structure with a threaded base. The handle can also include curved structural ribs that can be seen when the handle cover is removed. The handle shown in FIG. 1C includes a mounting ring, a bottom cover, and a central cover. The mounting ring is configured to be a part of the core piece. The bottom cover provides a smooth exterior surface and covers the structural ribs. The central column with luer is common to both assemblies shown in FIGS. 1B and 1C.

FIGS. 1D-E illustrate an assembly of the hydraulic chamber and the implant inserter. The assembly begins after the inserter tool has been placed in the body of a patient. The inserter's cover is pulled away and the hydraulic chamber is drawn to a position above the threaded ring on the inserter's handle. FIGS. 1D-E illustrate one embodiment of the above assembly. This version has assemblies with the least number of parts.

FIGS. 1F-G illustrates another exemplary implant deployment assembly, according to some embodiments of the present invention. This embodiment is functionally identical to the one shown in FIGS. 1D-E. As illustrated, a sleeve has been added to surround the lower shell of the hydraulic chamber. It covers the heads of the steel ports and forms a smooth transition to the outer walls of the top of the chamber. The stent inserter shown in this assembly includes three parts so that all structural ribs are concealed. A physician can use two hands to mount the hydraulic chamber assembly to the inserter handle. One hand can grasp the main body while the second hand holds the rotating collar in its upward position. The base of the column exposed below the collar nests in a ring inside the circle of threads on the stent inserter handle.

FIGS. 1H-I illustrates further steps in assembling the above system. When the chamber is seated on the inserter's ring, the threaded collar on the chamber assembly is dropped and turned to join chamber to stent handle, as illustrated by the arrows in FIG. 1H. FIG. 1I illustrates a completed assembly.

FIG. 1J illustrates insertion of an exemplary actuation rod for deployment of an implant disposed at the distal end of the cannula, according to some embodiments of the present invention. The actuation rod is inserted into the hydraulic chamber and turned to engage the threads in the stent assembly (FIG. 1K). The secondary knob on the rod can be engaged to the threads on the exposed piston shaft at the discretion of the physician (or other medical professional). That engagement is needed only if the implant collapse procedure (i.e., reduction of the implant size and its removal from the body) is to be carried out.

Figure 2A:
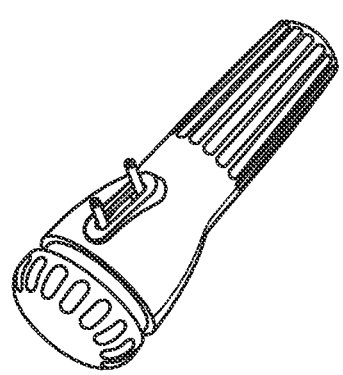
FIGS. 2A-C illustrate an exemplary power assembly for the system shown in FIGS. 1A-K, according to some embodiments of the present invention.
Figure 2B:
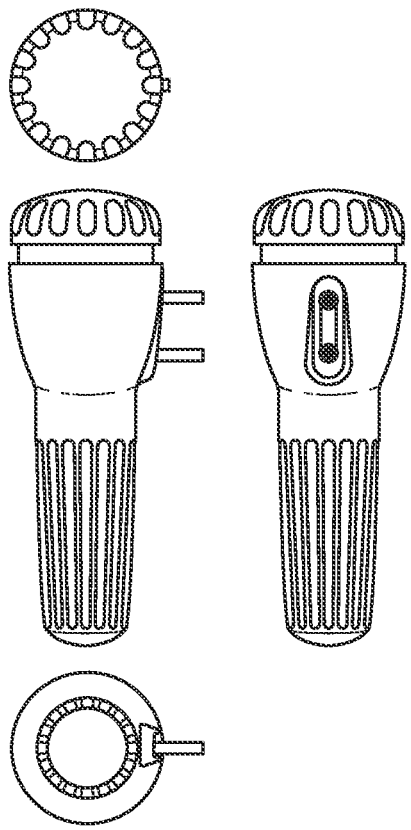
Figure 2C:
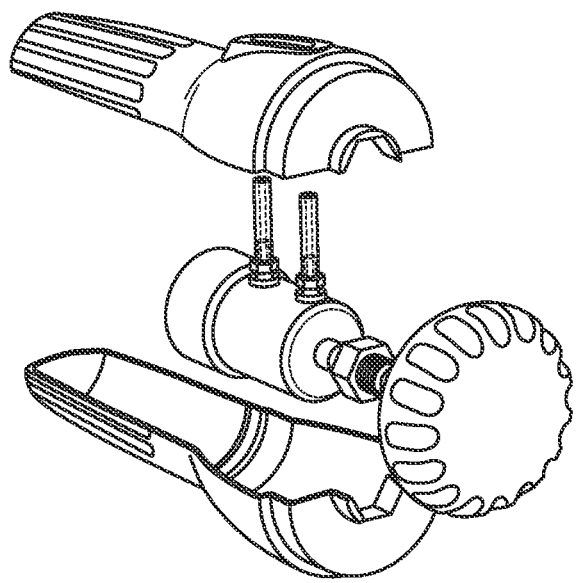

FIGS. 2A-C illustrates an exemplary power assembly, according to some embodiments of the present invention. The power assembly a housing and a cap or a turning knob enclosing the assembly and two tubes extending from the housing. FIG. 2A is a perspective view. FIG. 2B illustrates a top view, two side views and a bottom view of the power assembly. FIG. 2C illustrates an exploded view of the power assembly. To install and operate the power assembly, a physician can grasp the turning knob (along the centerline through the palm and curved fingers of the physician's grasping hand). The assembly includes a piston with a shaft along with a hydraulic chamber and a plurality of tubing extending from the chamber to the outer surface of the power assembly (as shown in FIG. 1K).

Figure 3A:
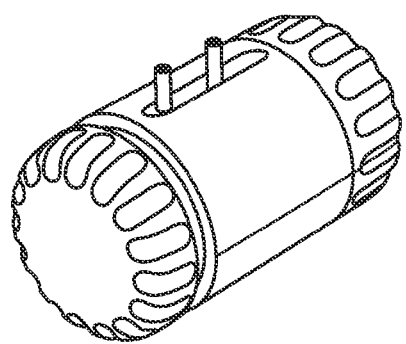
FIGS. 3A-C illustrate another exemplary power assembly for the system shown in FIGS. 1A-K, according to some embodiments of the present invention.
Figure 3B:
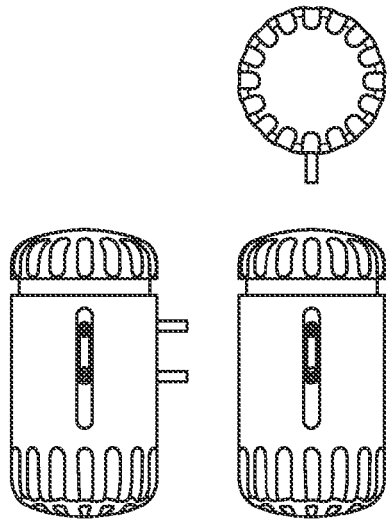
Figure 3C:
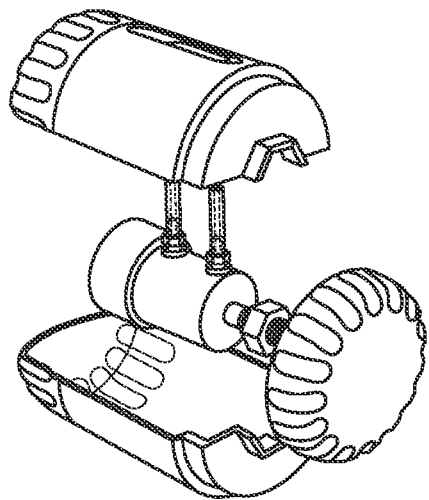

FIGS. 3A-C illustrate alternate exemplary embodiment of the power assembly, according to some embodiments of the present invention. The illustrated assembly has a cylindrical shape. In this embodiment, physician's palms can face each other to generate power for the hydraulic movement. This assembly can be used in a horizontal position or turned to a position that is nearly vertical.

Figure 4A:
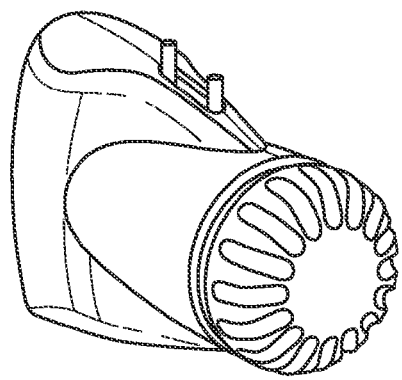
FIGS. 4A-C illustrate yet another exemplary power assembly for the system shown in FIGS. 1A-K, according to some embodiments of the present invention.
Figure 4B:
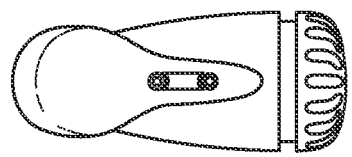
Figure 4B:
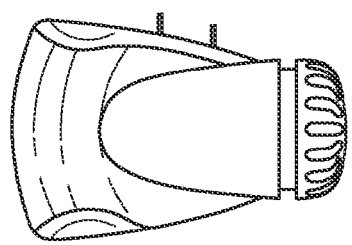
Figure 4B:
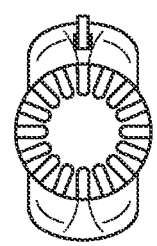
Figure 4C:
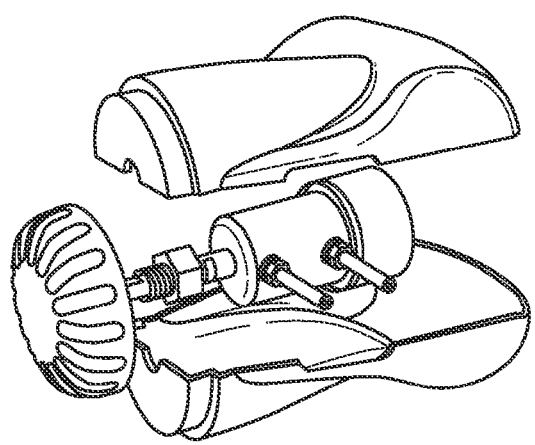

FIGS. 4A-C illustrate yet another exemplary embodiment of the power assembly, according to some embodiments of the present invention. The illustrated assembly has a cylindrical top portion and a substantially flat bottom portion. In this embodiment, physician's grasping hand holds the cylindrical shaped top portion with a centerline perpendicular to the knob's axis of rotation.

Figure 5E:
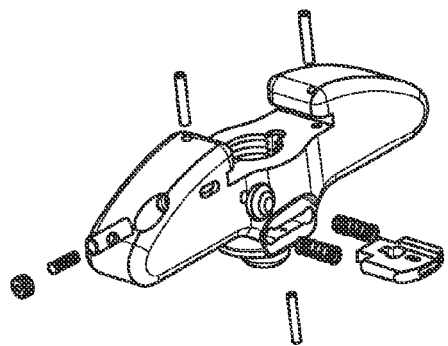

FIGS. 5A-I illustrate another exemplary embodiment of an implant deployment system, according to some embodiments of the present invention. FIG. 5A is an exploded perspective view of the system 500. The system 500 includes an implant 502 disposed at a distal end of an inserter cannula 502. A proximate end of the inserter cannula is coupled to an inserter handle 506. FIG. 5E is an exploded view of the inserter handle 506. The handle 506 includes threaded bore for securing the handle to the cannula. The handle 506 also includes an additional spring loaded shaft locking mechanism for interlocking the shaft disposed within the cannula. The inserter handle 506 is mounted on a central shaft 514 and is secured using a threaded knob 508. The system further includes a hydraulic power chamber 510 also coupled to the shaft 514. The chamber 510 is coupled to the handle 512. The handle 512 is further illustrated in FIGS. 5B-D. The handle 512 is further secured to an actuation rod 516 that includes a finger grip portion 518.

Figure 5F:
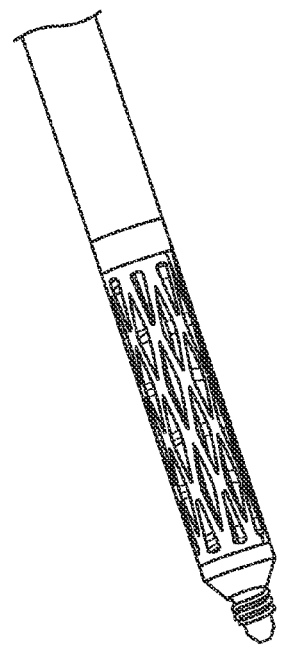
Figure 5G:
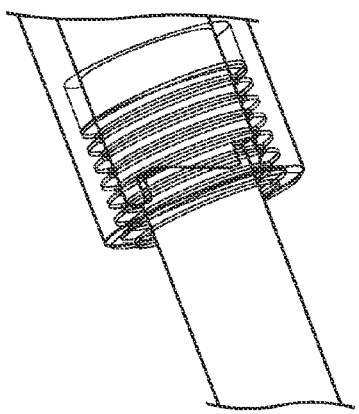
Figure 5H:
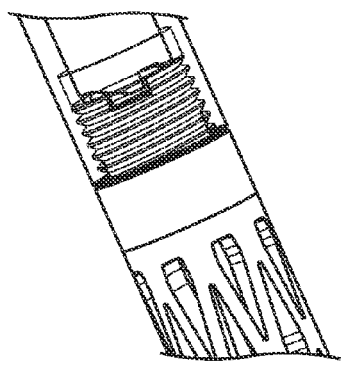
Figure 5I:
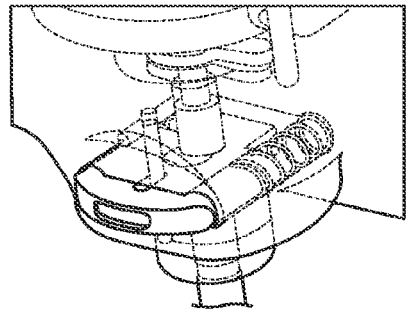

FIG. 5F illustrates implant 502 disposed at the distal end of the inserter cannula 504. Exemplary implants are illustrated in FIG. 13. FIGS. 5G-H illustrate coupling of the implant to the inserter cannula. FIG. 5I is a perspective cross-sectional view of the connection of the inserter cannula to the inserter handle.

FIGS. 6A-D illustrate an exemplary actuator handle assembly 600. FIG. 6A is a perspective view. FIG. 6B is a side view. FIG. 6C is a top view and a cross-sectional view taken along line A-A in FIG. 6B. FIG. 6D is an exploded perspective view. Referring to FIG. 6D, the assembly includes an outer cylinder (1), a thrust nut (2), a jack screw (5), an actuator handle (6), and a plurality of washers and circular clips (3), (4), (7), (8). To assembly the assembly 600, the jack screw (5) is placed into the outer cylinder (1) and secured with the clip (8). Then, the thrust nut (2) is threaded over the jack screw (5) and the thrust washer (3) is placed onto the thrust nut (2) and secured with the clip (4). The handle (6) is installed over the thrust nut (2) and secured with the clip (7). In some embodiments, the handle (6) can be oriented 90 degrees from outer cylinder tabs when the device is oriented in a counterclockwise position.

Figure 7A:
FIGS. 7A-C are various views of an exemplary implant actuation rod component of the system for deployment of an implant, according to some embodiments of the present invention.
Figure 7B:
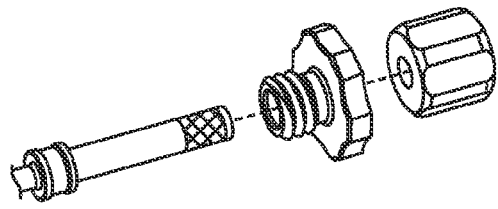
Figure 7C:
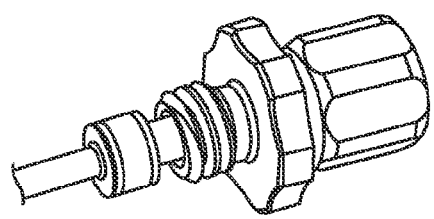

FIGS. 7A-C illustrate an exemplary implant actuator rod 700. FIG. 7A is a side view. FIG. 7B is an exploded perspective view. FIG. 7C is a perspective view. Referring to FIG. 7B, the actuator rod 700 includes an implant actuation rod shaft (1) coupled to a first implant actuation rod knob (2), which in turn is secured to the second knob (3), as shown in FIG. 7C. As can be understood by one skilled in the art, the rod shaft (1) can have any desired length.

Figure 8A:
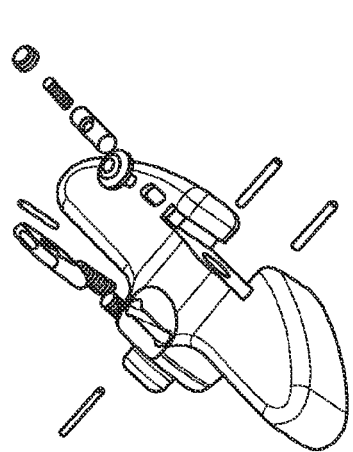
FIGS. 8A-C are various views of an exemplary implant inserter quick connect handle component of the system for deployment of an implant, according to some embodiments of the present invention.
Figure 8B:
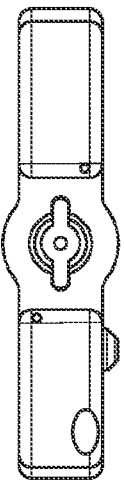
Figure 8C:
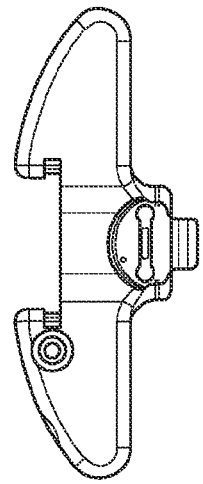
Figure 10:
FIGS. 10-11 are various views of an exemplary implant inserter quick connect handle of the system for deployment of an implant, according to some embodiments of the present invention.
Figure 10:
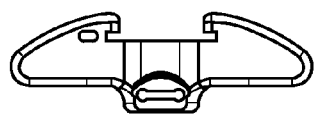
Figure 10:
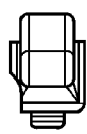
Figure 10:
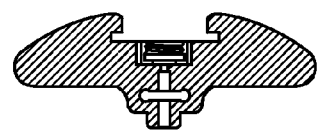
Figure 10:
Figure 11:
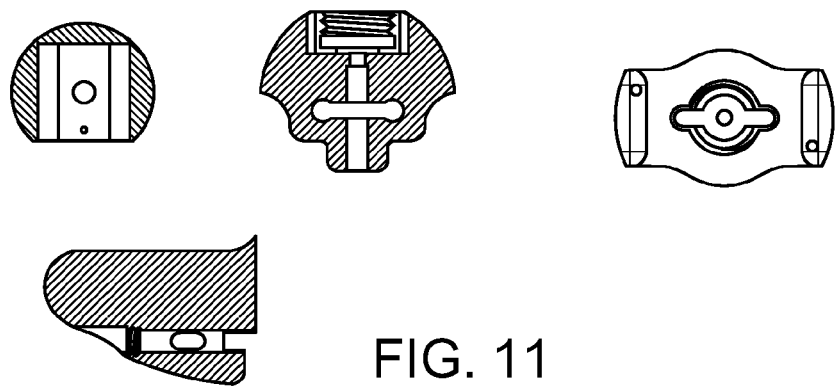

FIGS. 8A-C illustrate an exemplary implant inserter quick connect handle assembly 800, according to some embodiments of the present invention. FIG. 8A is a perspective view of the assembly 800. FIGS. 8B and 8C are top and side views of the handle, respectively. Referring to FIG. 8A, the assembly 800 includes a handle (1), a locking mechanism (2) coupled to a locking spring (8), a latching mechanism that includes a latch button (3), a latch shaft (4), a latch set screw (5), and a latch spring (9), and locking pins (6) and (7). As illustrated in FIG. 5A, the assembly 800 is coupled to the cannula 504. FIGS. 10-11 provide additional details of the assembly 800. As can be understood by one skilled in the art, the various dimensions illustrated in FIGS. 10-11 relating to different parts of the handle assembly 800 are provided here for exemplary, non-limiting purposes only.

Figure 9A:
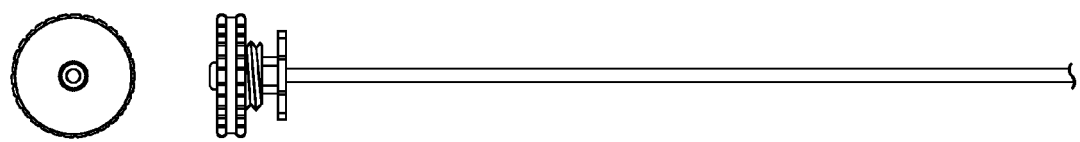
FIGS. 9A-B are various views of an exemplary implant inserter locking tube of the system for deployment of an implant, according to some embodiments of the present invention.
Figure 9B:
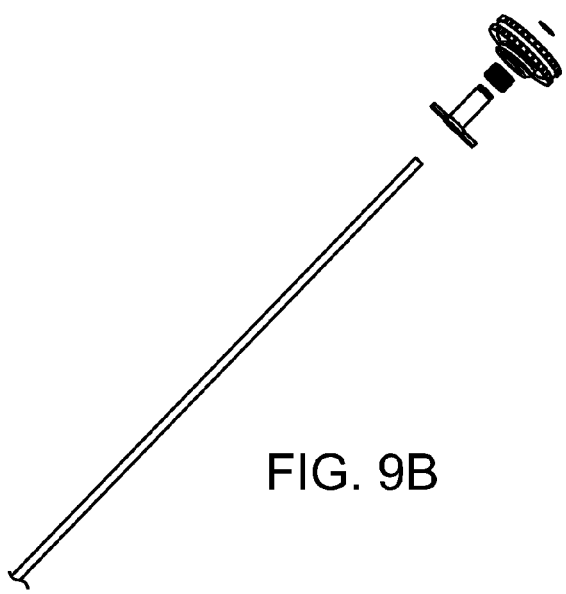

FIGS. 9A-B illustrate an exemplary implant inserter locking tube assembly 900, according to some embodiments of the present invention. FIG. 9A is a side view of the assembly 900. FIG. 9B is an exploded perspective view of the assembly 900. Referring to FIG. 9A, the assembly 900 includes a locking tube body (1) coupled to a locking tube shaft (2) and a locking tube knob (3) via a wave spring (5). The knob (3) is further coupled to the snap ring (4). The assembly (900) is secured to the handle assembly (800) illustrated above.

Figure 12A:
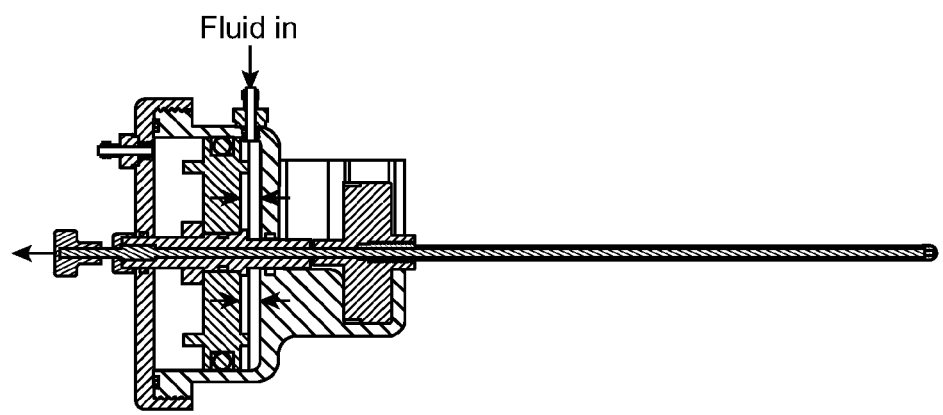
FIGS. 12A-B are cross-sectional views of an exemplary implant inserter, according to some embodiments of the present invention.
Figure 12B:
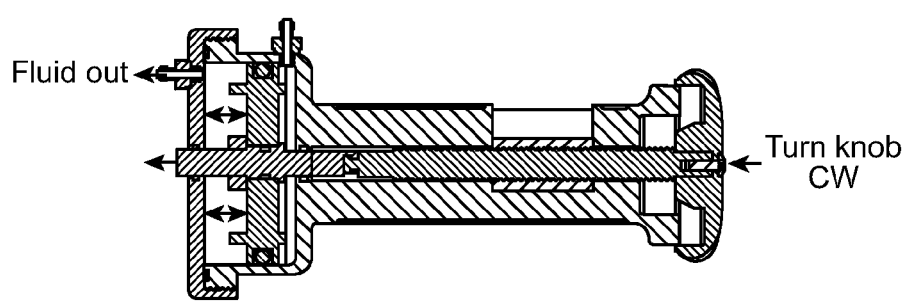
Figure 13:
FIG. 13 illustrates various implants in undeployed and deployed states.
Figure 13:
Figure 13:
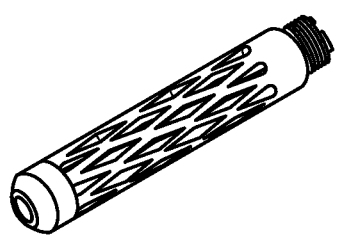
Figure 13:
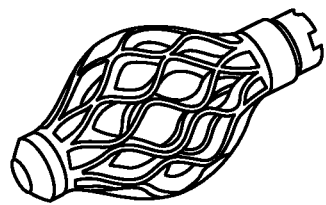
Figure 13:
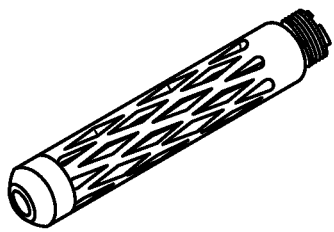
Figure 13:
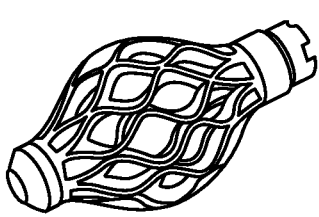
Figure 13:
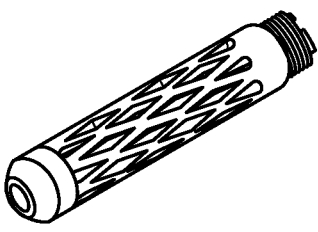
Figure 13:
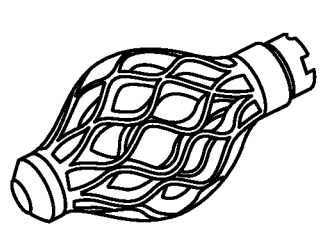

FIGS. 12A-B illustrate another exemplary embodiment of the implant deployment assembly, according to some embodiments of the present invention.

Exemplary implants are illustrated in FIG. 13, showing three embodiments, designated by 4.5 mm, 5.5 mm and 7.0 mm, in the undeployed and deployed configurations. During implantation, the implant diameters are expanded, and the expansion also reduces the length of the implant. For example, the 4.5 mm undeployed model has an initial diameter of 4.5 mm with an initial length of 26.4 mm, after expansion, the 4.5 mm deployed model has a maximum deployment diameter of 11.4 mm and a final length of 22.8 mm. The 5.5 mm undeployed model has an initial diameter of 5.5 mm and an initial length of 30.0 mm, after expansion, the 5.5 mm deployed model has maximum deployment diameter of 13.0 mm and a final length of 26.4 mm. The 7.0 mm undeployed model has an initial diameter of 7.0 mm and an initial length of 35.2 mm, after expansion, the 7.0 mm deployed model has a maximum deployment diameter of 14.8 mm and a final length of 31.7 mm. In the examples shown, the maximum deployed diameter is over twice the initial or undeployed diameter.

FIGS. 14A-14EE illustrate an exemplary surgical technique/method for deploying an implant, according to some embodiments of the present invention. The implant is a structural implant that acts as a scaffold to facilitate the stabilization and reduction of spinal fractures, creation of bony channels that allows for cement interdigitation within the cancellous bone, controlled implant deployment delivers reproducible results, and potential for less cement usage as compared to other systems. The method for deploying an implant can be used with the above system (also referred to as an OSSEOFIX Spinal Fracture Reduction System). The OSSEOFIX Spinal Fracture Reduction System is designed to facilitate the correction/reduction of spinal fractures (from T1-L5) by providing internal fixation and stabilization using an implant in conjunction with polymethylmethacrelate ("PMMA"). The system includes a range of implant sizes to provide the versatility required to match patient's anatomy. The implants may be manufactured from a combination of surgical grade titanium alloy and commercially pure titanium with an electrolytic conversion coating. In the examples shown, the implant is intended for use in the thoraco-lumbar spine.

Preoperative Implant Sizing—Prior to performing the implant procedure, review patient X-Rays to determine the appropriate sized implant(s) to use.

FIGS. 14A-14BB illustrate a surgical approach method using an access cannula. FIGS. 14CC-14DD illustrate a surgical approach method using a k-wire.

Referring to FIG. 14A, the method begins with inserting a working cannula assembly, using fluoroscopic guidance, through the pedicle to the desired depth inside of a vertebral body. Once the position of the working cannula assembly has been confirmed with fluoroscopy, the working cannula trocar is unthreaded and removed from the working cannula, as shown in FIG. 14B. The working cannula can serve as an access channel, into the vertebral body, throughout the procedure. Then, as shown in FIG. 14C, a drill is inserted through the working cannula and drill to desired depth.

As shown in FIG. 14D, the implant inserter is assembled by attaching the quick connect handle to implant inserter cannula. The two components should match for proper operation. The loading button is pushed and the implant inserter cannula is then inserted. In some embodiments, the implant inserter can include a reference line that is lined up with the loading button on the quick connect handle. Once the implant inserter cannula has been inserted, the loading button locking the two pieces into place is released. A physician can confirm that the quick connect handle is locked securely in place. To unlock the implant inserter cannula from the quick connect handle, the loading button can be pushed and the implant inserter cannula can be removed.

Figure 14F:
Figure 14G:
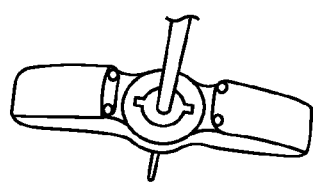

As shown in FIG. 14E the locking tube is identified and threaded into the implant inserter ensuring a tight fit. As shown in FIG. 14F-G, a t-bar can be included on the underside of the locking tube. The t-bar can include a depression located on the top side of the quick connect handle. The t-bar depression and the handle are aligned when placing the locking tube onto the implant inserter and threading the two components together.

Figure 14H:

In some embodiments, the implants used with the above assemblies can be identified using a color-scheme. For example, as illustrated in FIG. 14H-I, an implant is identified by ensuring that its color matches color bands on implant inserter. Then, the implant is lightly threaded onto the distal tip of the implant inserter. In some embodiments, an audible click can be heard confirming that the implant is threaded properly into place. No torque should be applied when threading the implant onto the shaft. The locking tube will ensure a secure attachment between the implant and the implant inserter.

Figure 14N:
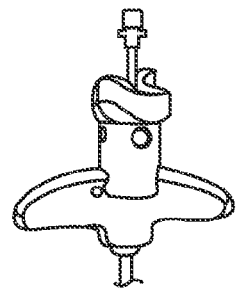
Figure 14I:
Figure 14O:
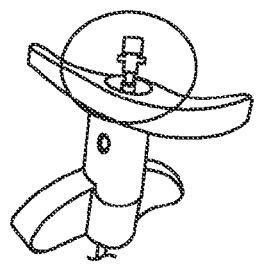
Figure 14J:
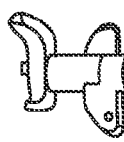
Figure 14K:
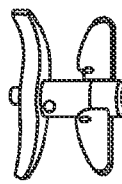

As shown in FIG. 14J-K, the actuator is positioned perpendicular to and on top of the implant inserter handle. Then, the actuator is locked onto the implant inserter handle by rotating the fluted metal shaft of the actuator in the clockwise direction. In some embodiments, a click can be heard once the actuator is positively engaged with the quick connect handle. As shown in FIG. 14L-M, the actuator is then fully turned in a counterclockwise direction.

Further to the above color-identification scheme, the correct actuation rod can be identified by matching the color band on the actuation rod to the color band on the implant inserter, as shown in FIG. 14N. Then, the actuation rod is inserted through the actuator into the implant inserter.

As shown in FIG. 14O, a physician can confirm that the two knobs on the actuation rod are in contact. Then, the actuation rod is threaded into the implant by rotating the black knob clockwise until no more rotation occurs. Once the black knob is fully engaged, the metal knob is rotated clockwise until fully engaged.

Figure 14P:
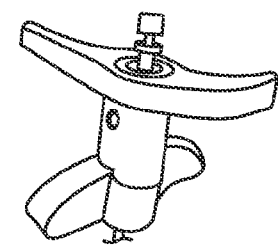
Figure 14L:
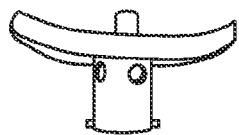
Figure 14M:
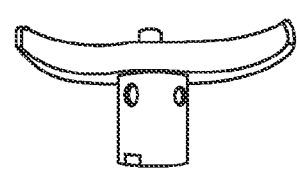

FIG. 14P illustrates the actuation rod fully threaded into place when the metal clip on the actuation rod can no longer be rotated in a clockwise direction. In some embodiments, the tip of the actuation rod can be seen protruding out of the distal end of the implant.

Figure 14Q:
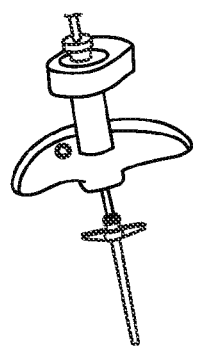
Figure 14R:
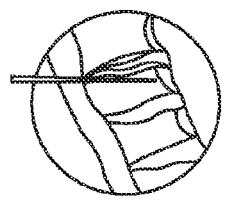

Then, the implant inserter assembly is placed through the working cannula into the vertebral body, as shown in FIGS. 14Q-R. The position of implant can be confirmed with fluoroscopy prior to implant deployment (as shown in FIG. 14R).

Figure 14S:
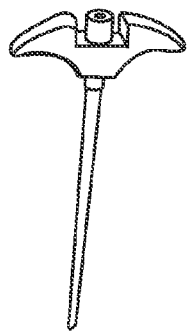
Figure 14S:
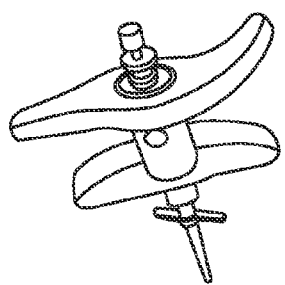
Figure 14W:
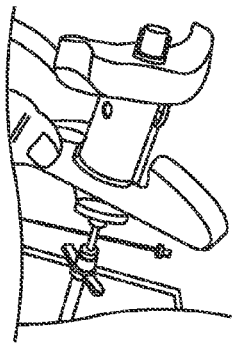
Figure 14T:
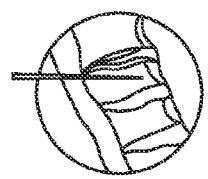

FIG. 14S-T illustrate implant deployment. While referencing fluoroscopic imaging (FIG. 14T), the actuator is rotated in a clockwise direction to deploy the implant. The color band on the actuator can become visible as the actuator is rotated. Once the desired degree of implant deployment has been achieved, rotation of the actuator is stopped. A stop mechanism can be built into the actuator to prevent over-deployment of the implant. In some embodiments, the actuator can be turned 3.5 turns before the stop mechanism is engaged.

Figure 14X:
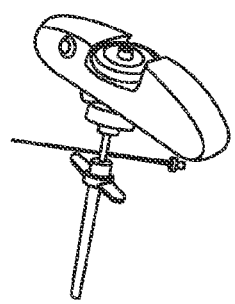
Figure 14U:
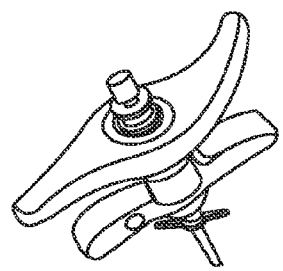

FIG. 14U illustrates implant repositioning. If repositioning of the implant is desired, the implant inserter is rotated in a counterclockwise direction, while using live fluoroscopic imaging, until the implant is compressed. The implant can be repositioned to a desired location and then redeployed, if desired. Redeploying procedure can be performed as illustrated in FIGS. 14O-T. In some embodiments, the implant can be compressed to approximately 75% of its deployed size. In some embodiments, the implant should not be compressed and redeployed more than once.

Figure 14Y:
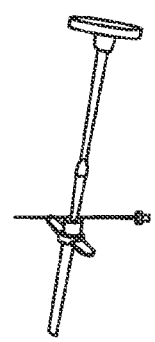
Figure 14V:
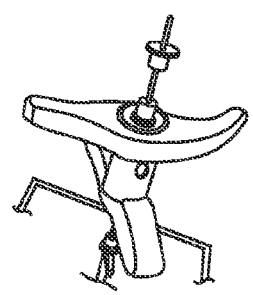

FIG. 14V illustrates a disassembly procedure. To disassemble, the actuator is rotated a quarter turn in the counterclockwise direction. Then, the actuation rod is disengaged from the implant inserter by rotating a first metal knob and then a second knob in a counterclockwise direction. Then, the actuation rod is removed.

FIG. 14W illustrates an actuator removal procedure. To remove the actuator, a metal latch disposed on the actuator is pulled in a direction identified on the actuator. While holding back the trigger, the actuator is rotated 90 degrees in a counterclockwise direction and then disengaged from implant inserter. Then, the actuator can be removed.

Then, implant inserter handle and the locking tube can be disengaged from the implant inserter cannula by compressing the loading button and pulling upwards, as shown in FIGS. 14X-Y. The implant inserter handle is then removed.

Figure 14Z:
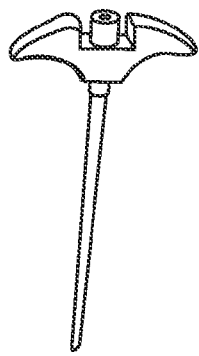
Figure 14C:
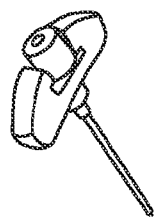
Figure 14A:
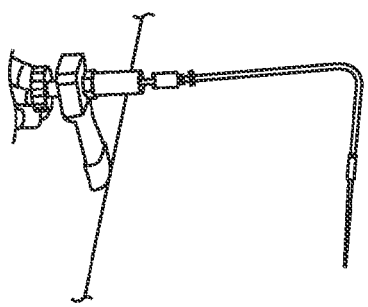
Figure 14D:
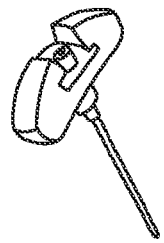
Figure 14B:
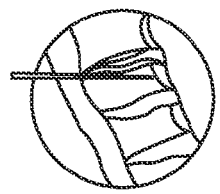
Figure 14E:
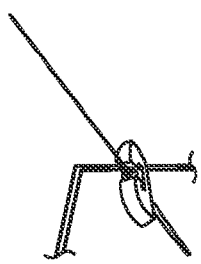

FIG. 14Z illustrates a bone biopsy procedure. In some embodiments, a bone biopsy cannula is placed through the implant inserter cannula and rotated slightly from side to side to capture a bone core. Then, the bone biopsy cannula and the bone core are removed by inserting bone biopsy obturator through the bone biopsy cannula. This procedure can be repeated until desired volume of bone has been removed.

FIGS. 14AA-BB illustrate an exemplary cement delivery procedure. In some embodiments, a PMMA bone cement is mixed in accordance with packaging or other instructions with the bone cement. Once the cement has been mixed to the desired consistency, the delivery system is lure locked to the proximal end of the bone biopsy cannula. Then, a desired amount of cement is injected into the implant. The cement delivery can be verified under live fluoroscopy. Bone biopsy cannula can be removed after cement delivery has been completed and the implant inserter cannula can be unthreaded from the implant.

As stated above, FIGS. 14CC-EE illustrate an alternate embodiment of a surgical approach using a k-wire. The procedure includes steps of inserting a targeting needle through the pedicle into the vertebral body, removing targeting needle trocar, and insert k-wire through targeting needle to desired depth inside vertebral body. This procedure can be followed by the steps illustrated in FIGS. 14A-14BB. Upon completion of steps shown in FIGS. 14H-I, the implant inserter is placed over the k-wire into the vertebral body.

FIG. 15 illustrates instruments used in connection with surgical deployment procedures shown in the different embodiments, including a targeting needle, K-Wire, working cannula introducer, drill, locking tube, quick connect handle, actuator, actuation rod and bony biopsy cannula.

Figure 16:
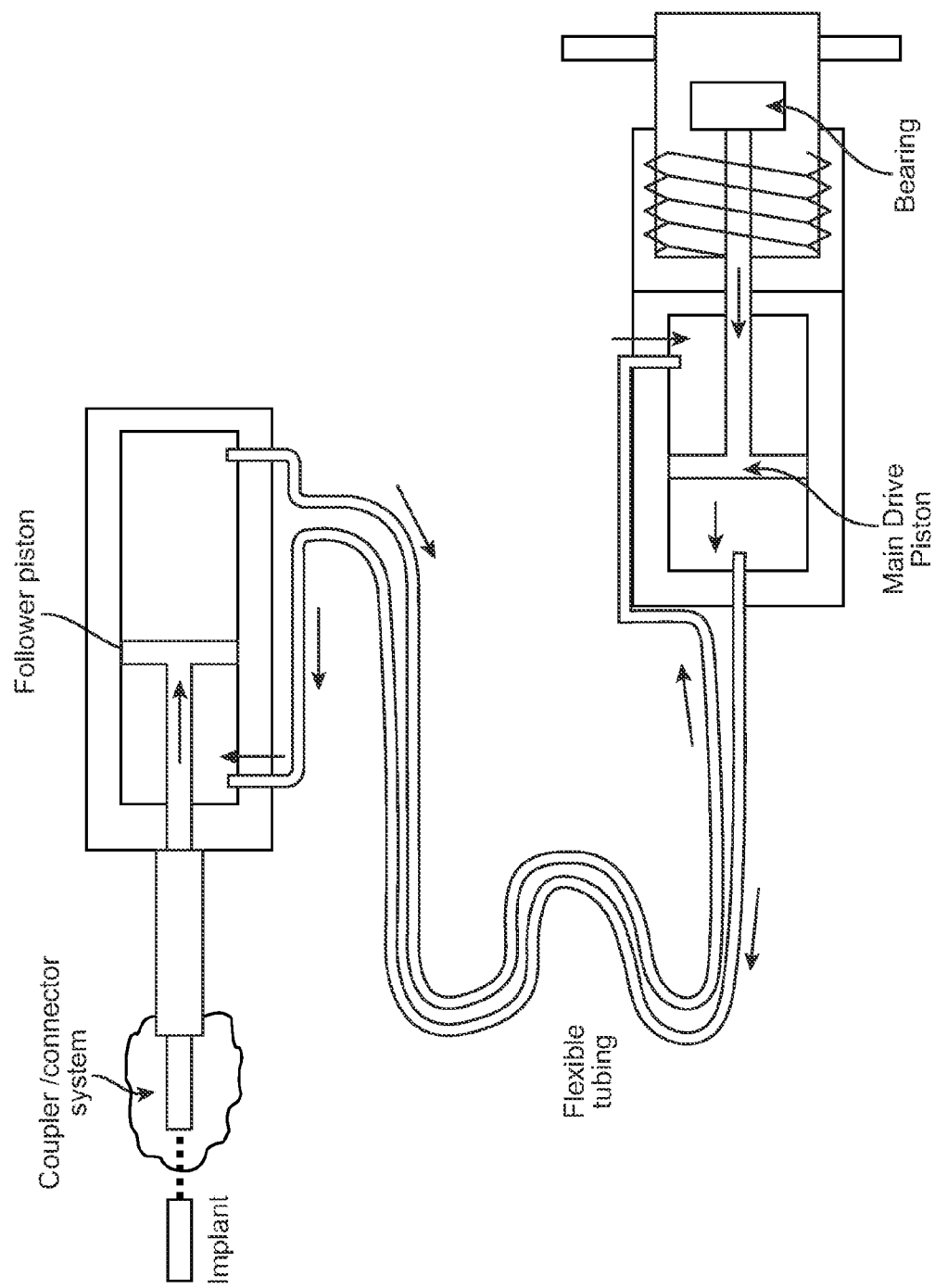
FIG. 16 illustrates an exemplary hydraulic system for insertion of an implant.

FIG. 16 illustrates an exemplary V-stent hydraulic system. The system includes a main drive piston component coupled to a follower piston using flexible tubing. The follower piston is coupled to the coupler/connector system. An implant is coupled to the coupler/connector system. The tubing can be used for expanding and contracting of the implant upon movement of the pistons. The direction of flow of air in the tubing for expansion can be reverse to the direction of flow during contraction. A screw mechanism can be implemented in the main drive piston for providing air. In some embodiments, the pistons can represent two closed systems.

FIGS. 17A to 17FF show another embodiment of a surgical technique of a spinal fracture reduction system.

Preoperative Implant Sizing—Prior to performing the implant procedure, review patient X-Rays to determine the appropriate sized implant(s) to use.

Figure 17A:
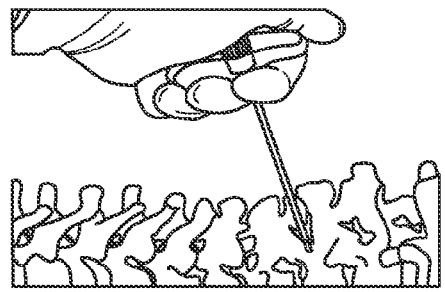
FIGS. 17A-17FF illustrate another exemplary spinal reduction/correction method, according to some embodiments of the present invention.
Figure 17B:
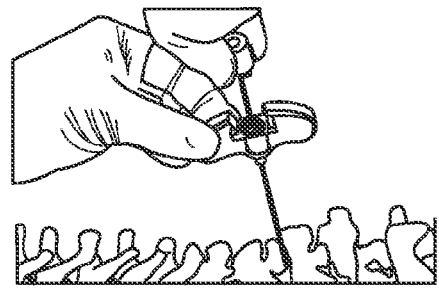
Figure 17C:
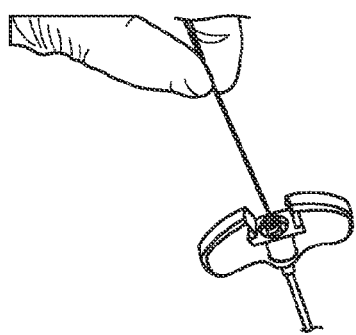

FIGS. 17A-17C show pedicle preparation. Prior to gaining access into the pedicle, the operative vertebral body needs to be identified, under fluoroscopy, in the AP plane. A combination of cranio-caudal and lateral augmentation of the C-arm is used to bring the pedicle within the vertebral body and between the endplates for proper alignment. Once proper C-arm alignment is achieved, the targeting needle is advanced into the bone stopping at the junction of the pedicle and vertebral body. Remove the targeting needle trocar. A small skin incision may be required to ease targeting needle insertion.

K-Wire placement. Using fluoroscopic guidance, place K-Wire through Targeting Needle into the vertebral body. Verify position of K-Wire, using fluoroscopy, throughout procedure. Ensure the K-Wire does not migrate when using the cannulated instrumentation.

Figure 17D:
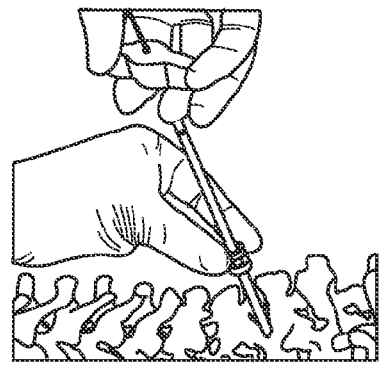

FIG. 17D shows vertebral body preparation. Place drill sleeve over K-Wire through the skin to the base of the pedicle to protect soft tissue from Drill. Insert Drill over K-Wire into drill sleeve. Rotate the drill clockwise to create pathway into the anterior third of the vertebral body, stopping a few millimeters posterior to the anterior cortex. A small skin incision may be required prior to placing the drill sleeve over the K-Wire.

Figure 17E:
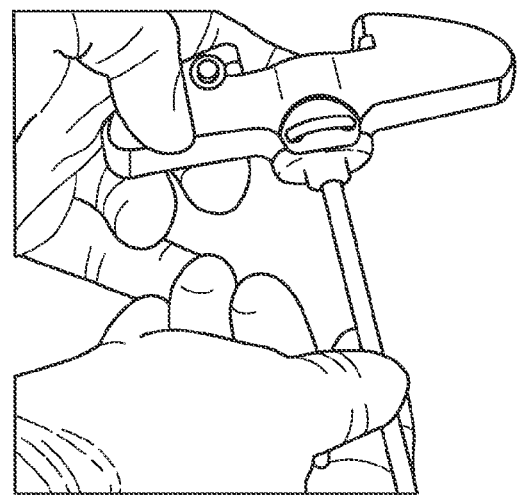
Figure 17F:
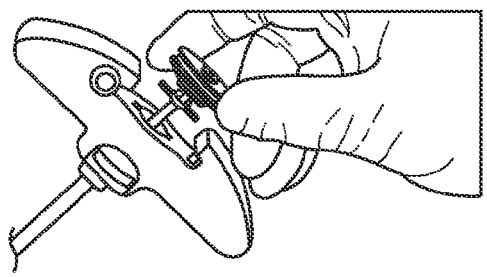
Figure 17G:
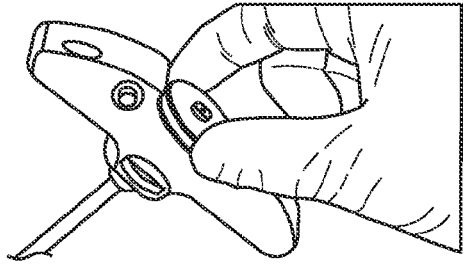
Figure 17H:
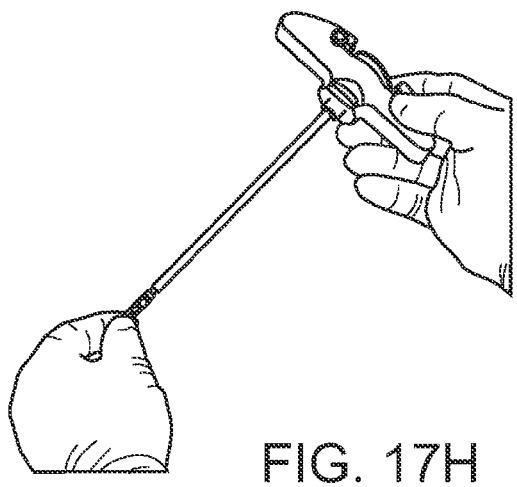

FIGS. 17E-17G show implant inserter assembly. Identify chosen implant by ensuring color of implant matches color bands on implant inserter. Push the loading button on the quick connect handle and insert the implant inserter cannula. Make sure the reference line on the implant inserter cannula lines up with the loading button on the quick connect handle. Once the implant inserter cannula has been inserted, release the loading button locking the two pieces into place. Confirm that the quick connect handle is locked securely in place. Identify the locking tube to be used by locating the color band on the circumference of the dial and confirming that it matches the color bands on the implant inserter and quick connect handle. Thread the locking tube into the quick connect handle until fully seated. Notice the t-bar located on the underside of the locking tube and the t-bar depression on the top side of the quick connect handle. Ensure that these align when placing the locking tube onto the implant inserter and threading the two components together FIG. 17H shows implant attachment. Identify the chosen implant by ensuring color of implant matches color bands on Implant Inserter. Lightly thread the implant onto the distal tip of the implant inserter. Audible clicks will be heard confirming the implant is engaged on the implant inserter. Do not torque the implant onto the shaft. The locking tube will ensure a secure attachment between the implant and the Implant Inserter.

Figure 17I:
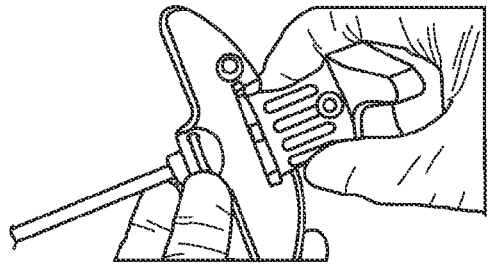
Figure 17K:
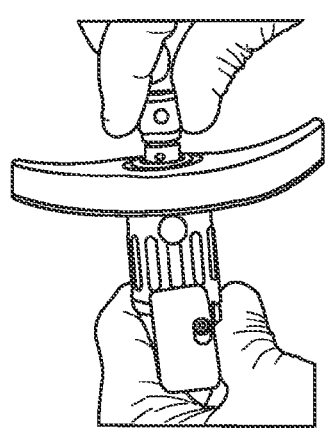
Figure 17J:
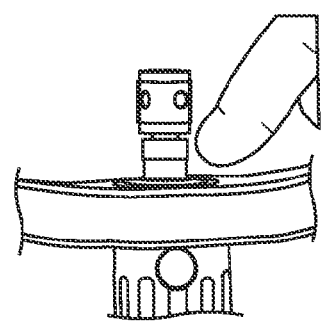

FIGS. 17I-17J show actuator attachment. Position the actuator perpendicular to and on top of the implant inserter handle. Lock the actuator onto the implant inserter handle by rotating the fluted metal shaft of the actuator in the clockwise direction. A click will be heard once the actuator is positively engaged with the quick connect handle. Place implant inserter assembly over K-Wire and into the vertebral body. Once implant inserter assembly has been placed, remove the K-Wire. If the red band is exposed (FIG. 17J), turn the actuator counterclockwise until it is no longer visible.

FIG. 17K shows identify the actuation rod. Identify the correct actuation rod by matching the color band on the actuation rod to the color band on the implant inserter. Advance the actuation rod through the actuator into the implant inserter. Rotate actuation rod until resistance is felt and the end is threaded into the implant. Depress the knob of the actuation rod into the key feature of the actuator. Rotate clockwise until a positive lock is achieved. Confirm that the tip of the actuation rod is seen protruding out of the distal end of the implant.

Figure 17L:
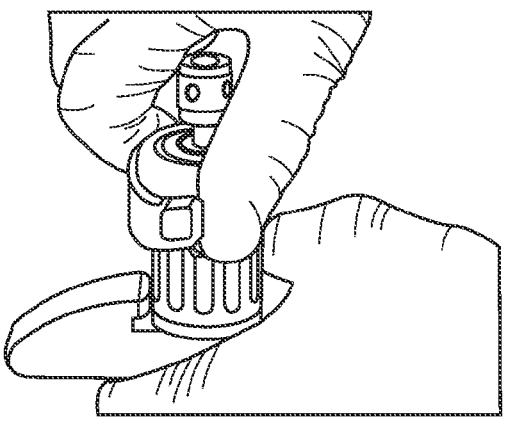

FIG. 17L shows implant deployment. While referencing fluoroscopic imaging in the lateral plane, rotate Actuator in a clockwise direction to deploy the implant. The red band on the actuator will become visible as the actuator is rotated and the implant is deployed. Once the desired degree of implant deployment has been achieved stop rotating the actuator. A stop mechanism has been built into the actuator to prevent overdeployment of the implant.

Figure 17M:
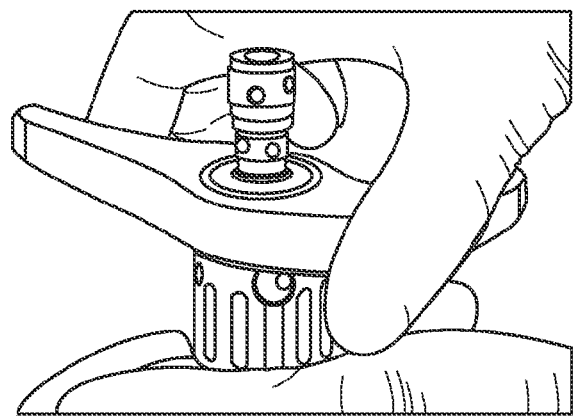

FIG. 17M shows implant repositioning. If repositioning the implant is required, rotate the implant inserter in a counterclockwise direction, while using live fluoroscopic imaging, until the implant is compressed. Reposition the implant to desired location and redeploy the implant. NOTES: The implant can only be compressed to approximately 75% of its deployed size. In most embodiments the implant can only be compressed and redeployed once.

Figure 17N:
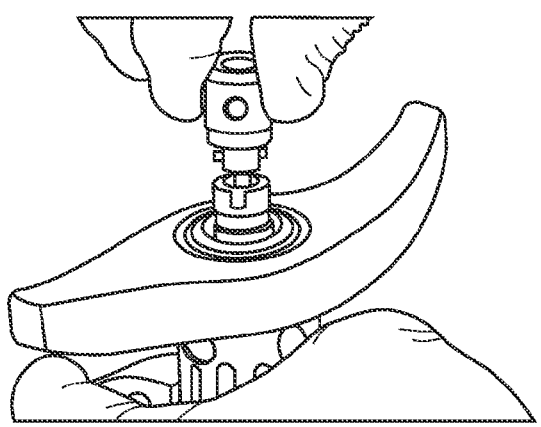

FIG. 17N shows actuation rod removal. To disassemble, depress the outer knob of the actuation rod and rotate counterclockwise until the actuation rod is released from the key feature of the actuator. Unthread and remove the actuation rod.

Figure 17O:
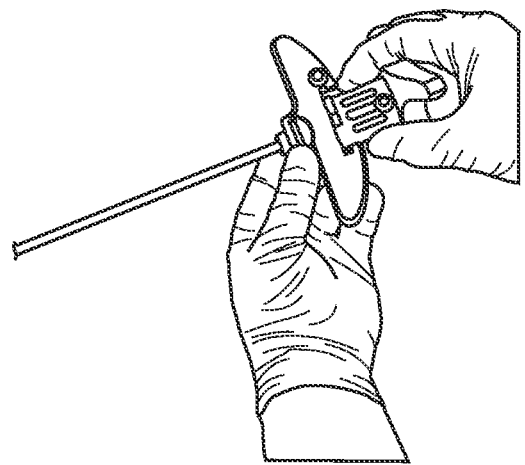

FIG. 17O shows actuator disassembly. To remove actuator, pull trigger in the direction identified by the arrow. While holding back the trigger, rotate the actuator 90 degrees in a counterclockwise direction and disengage from quick connect handle. Remove actuator.

Figure 17P:
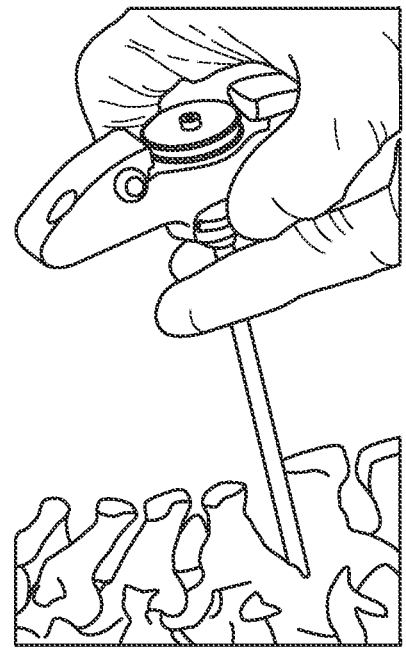

FIG. 17P shows implant inserter disengagement. Disengage quick connect handle and the locking tube from the implant inserter cannula by compressing the loading button and pulling upwards. Remove the implant inserter handle.

Figure 17Q:
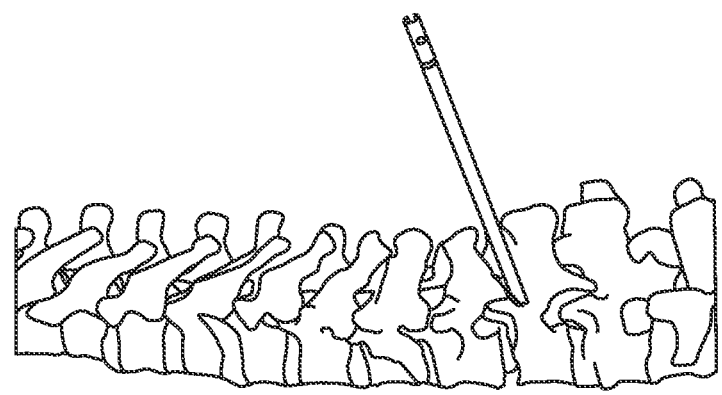

FIG. 17Q shows the working cannula in place.

Figure 17R:
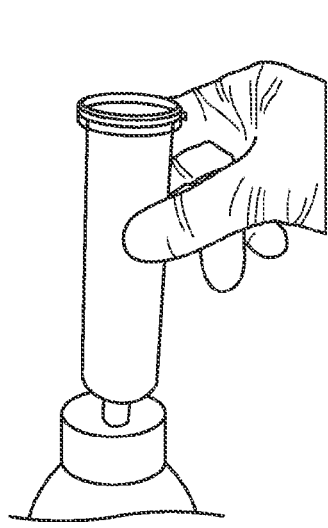
Figure 17S:
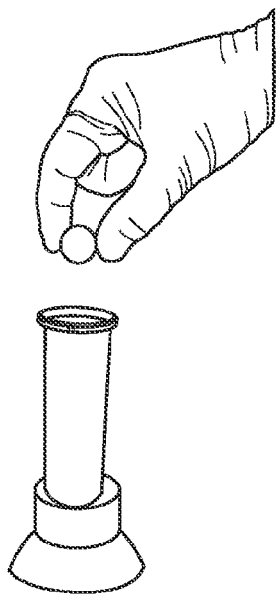
Figure 17T:
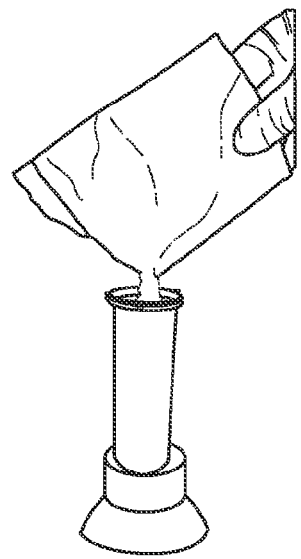
Figure 17U:
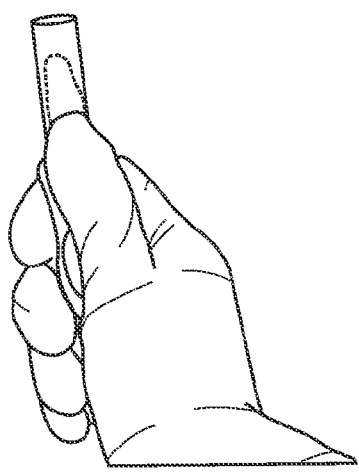
Figure 17V:
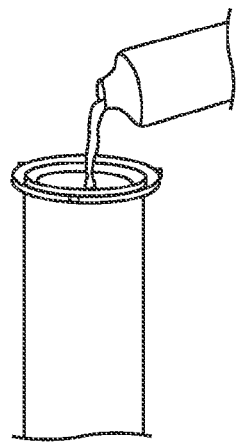
Figure 17W:
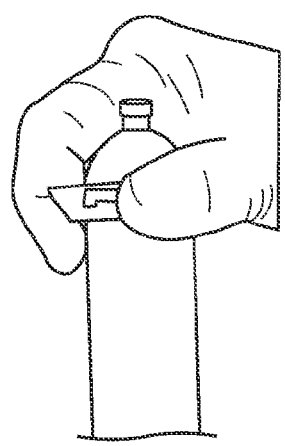
Figure 17C:
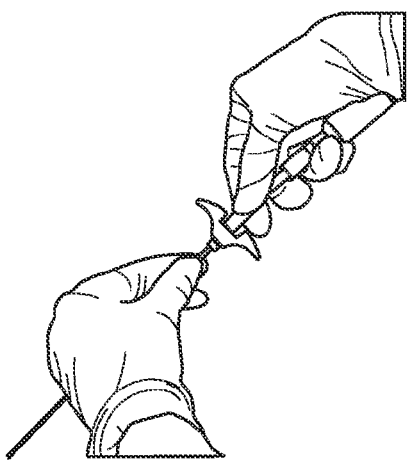
Figure 17D:
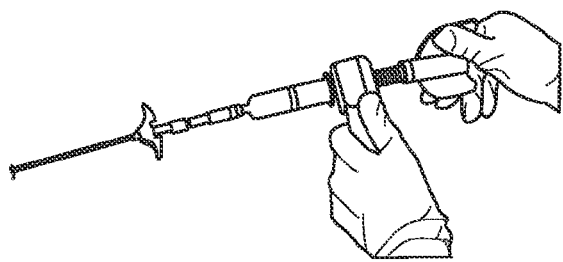
Figure 17E:
Figure 17F:
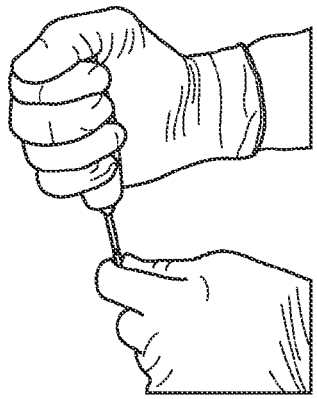

FIGS. 17R-17FF show cement mixing and delivery. Place mixing chamber onto base. Insert glass ball into mixing chamber. Pour PMMA powder into mixing chamber. Open monomer vial by snapping the neck of the bottle away from the white dot located on the monomer bottle. Pour liquid monomer into the mixing chamber. Place lid on top of mixing chamber and remove mixing chamber from base. Make sure the lid is locked in place. Place three fingers on the lid and shake mixing chamber up and down for 45 seconds. To extend cement working time, chill the mixing and delivery system, cement and monomer 1 hour prior to surgery.

For use, rotate mixing chamber 180° to ensure delivery valve is facing upward. Remove delivery cap from mixing chamber by rotating cap in counterclockwise direction. Luer lock cement delivery gun onto delivery valve. Rotate mixing chamber and cement delivery gun 180 degrees until the delivery valve is facing downward. rotate the knob on the cement delivery gun in a counterclockwise direction to draw up the desired amount of cement into the gun. To ensure the maximum volume of cement is drawn in the gun, continue turning the gun knob in a counterclockwise direction until resistance is met. Detach the cement delivery gun from the mixing chamber. Luer lock the short or long extension tube onto the cement delivery gun. Luer lock short or long extension tube onto cement delivery cannula. Be sure the luer connection is tightly threaded onto the cement delivery cannula and the cement delivery gun. Prime cement through the cement delivery cannula to bring cement to the tip of the cannula before inserting it through the implant inserter tube. Insert the cement delivery cannula through the implant inserter tube into the implant. Inject cement by rotating the knob on the cement delivery gun in a clockwise direction while verifying cement delivery under live lateral and AP fluoroscopy. Dosage: As required for adequate fixation of the pathological fracture. Stop injection as soon as sufficient cement has been placed to stabilize the fracture, or if cement reaches cortex, an endplate or if leakage is noticed. Rotate knob on the cement delivery gun one full rotation in a counterclockwise direction to relieve pressure. Notes: the cement may be a medium viscosity cement. Inject the cement by rotating the delivery gun knob a quarter turn at a time. Stop cement injection when cement delivery gun knob reaches the back of the cement delivery gun. Do not inject cement directly through the implant inserter tube into the implant.

Implant inserter cannula removal. once cement delivery is complete, unthread the implant inserter cannula from the implant. If the implant cannot be unthreaded from the implant inserter cannula, the countertorque should be used. Place the countertorque through the implant inserter cannula into the implant. Hold the countertorque stationary while unthreading the implant inserter cannula. Remove cement delivery cannula after cement delivery has been completed.

Figure 18A:
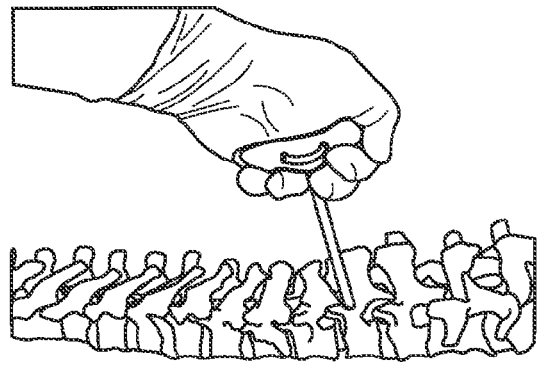
FIGS. 18A-18C illustrate another method, according to some embodiments of the present invention.
Figure 18B:
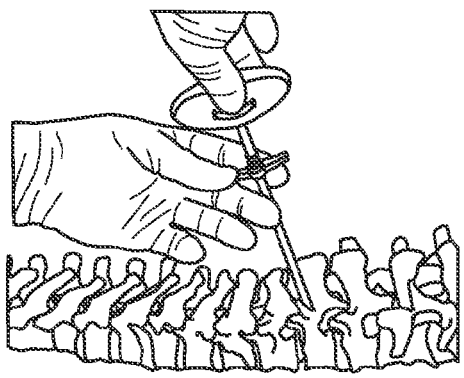
Figure 18C:
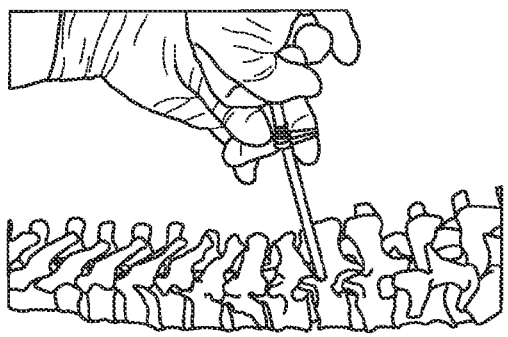

FIGS. 18A-18C show an alternate surgical approach working cannula technique. Accessing pedicle—prior to gaining access to the pedicle for the procedure, the vertebral body needs to be visualized in the AP plane. A combination of cranio-caudal and lateral augmentation is used to bring the pedicle within the vertebral body and between the endplates for proper visualization. The working cannula assembly is inserted through the pedicle and is placed just anterior to the posterior cortex. Once the position of the working cannula assembly has been confirmed with fluoroscopy, unthread the working cannula trocar and remove from the working cannula. The working cannula will serve as an access channel into the vertebral body throughout the procedure. A small skin incision may be required to ease targeting needle insertion. Vertebral body preparation—Insert drill through the working cannula. Create a pathway into the anterior third of the vertebral body. End the pathway a few millimeters posterior to the anterior cortex. Continue with the procedure shown above.

Figure 19A:
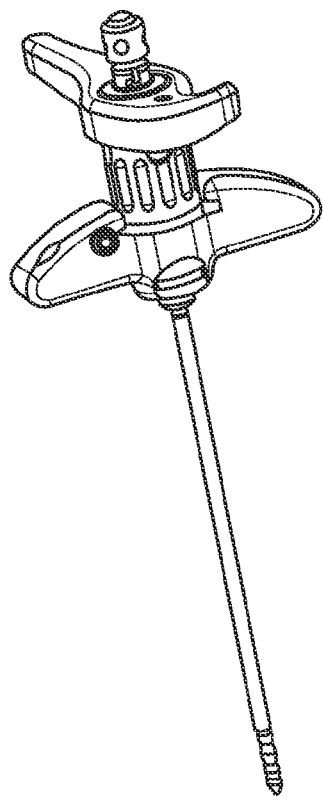
FIGS. 19A-19W are detailed views of another exemplary system for deployment of an implant, according to some embodiments of the present invention.
Figure 19B:
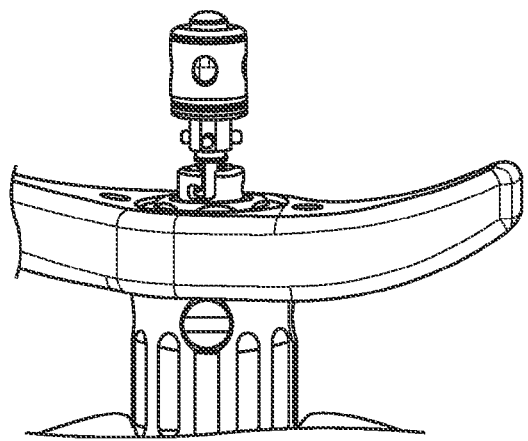
Figure 19C:
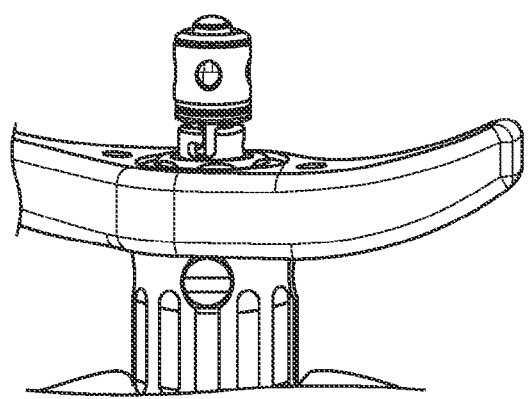
Figure 19D:
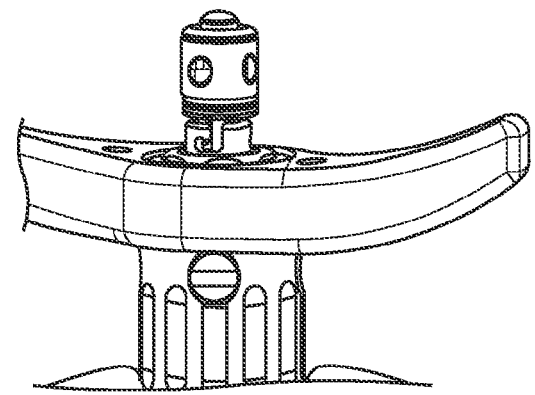
Figure 19E:
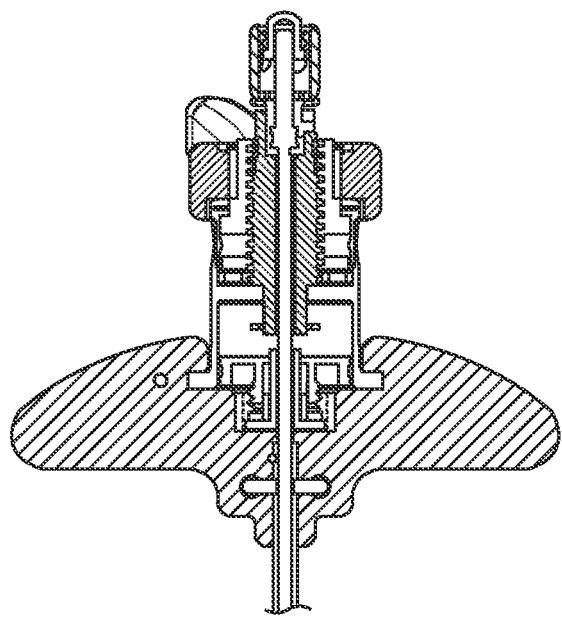
Figure 19F:
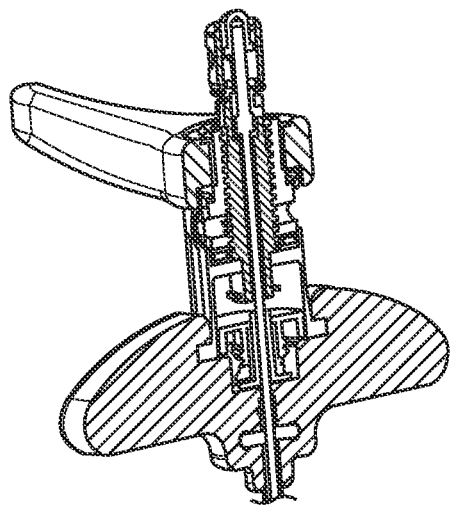
Figure 19G:
Figure 19H:
Figure 19I:
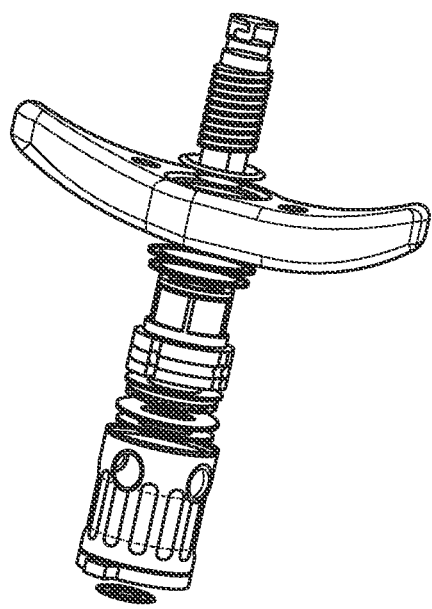
Figure 19J:
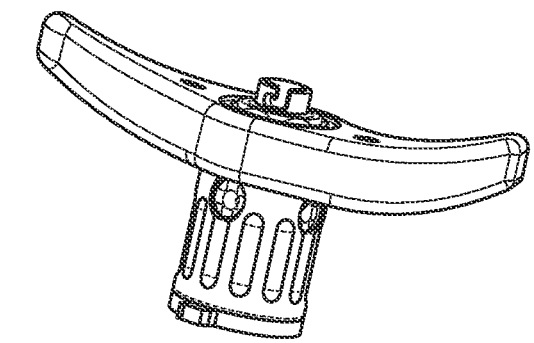
Figure 19K:
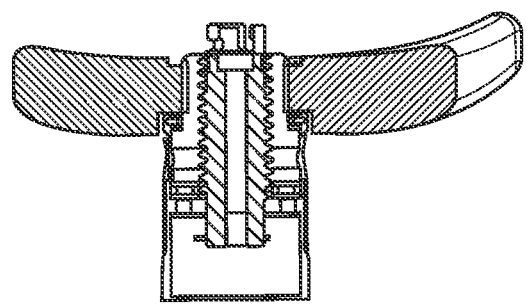
Figure 19L:
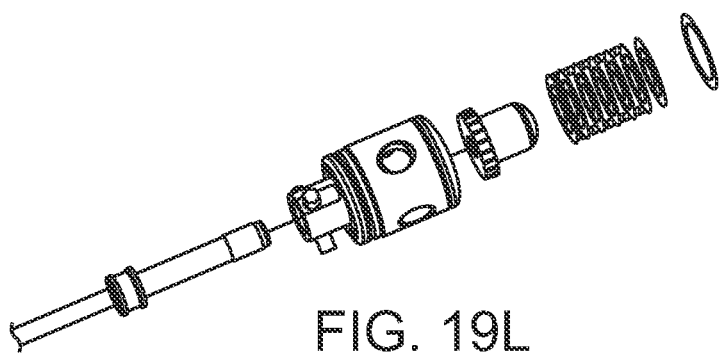
Figure 19M:
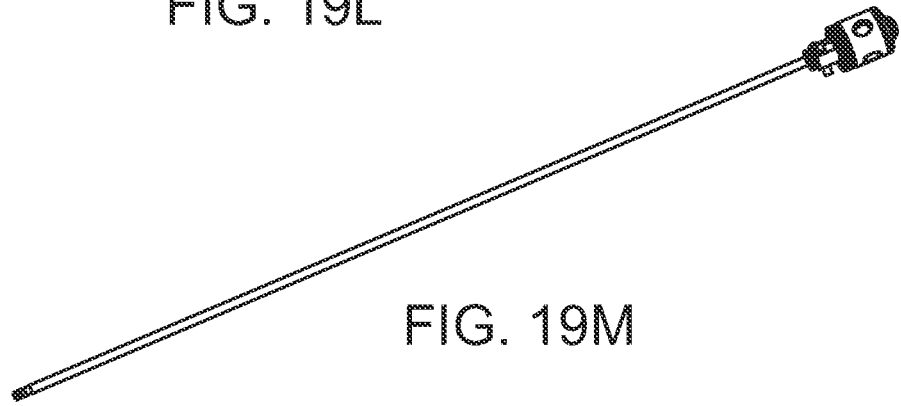
Figure 19N:
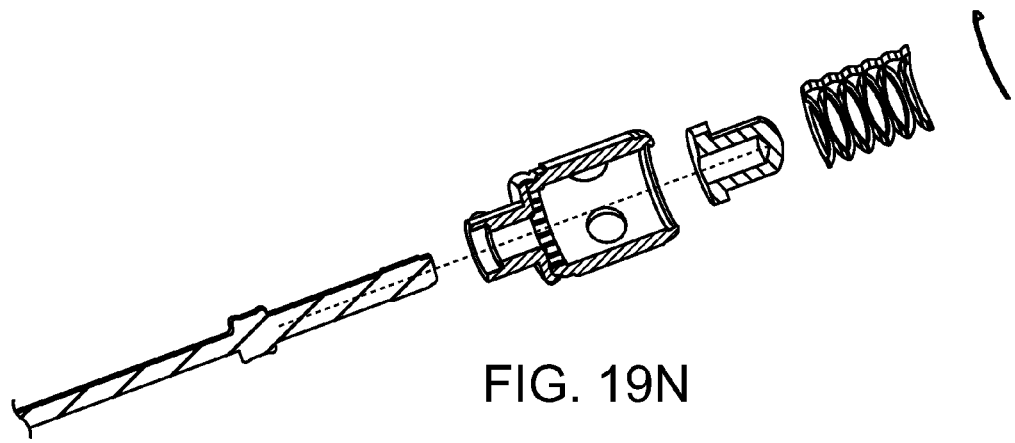
Figures 19O, 19P:
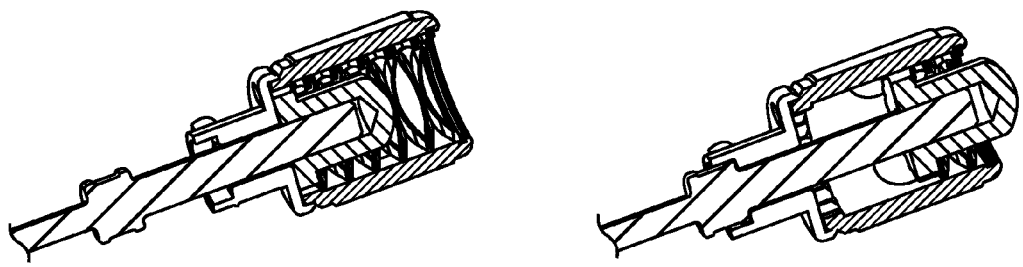
Figure 19Q:
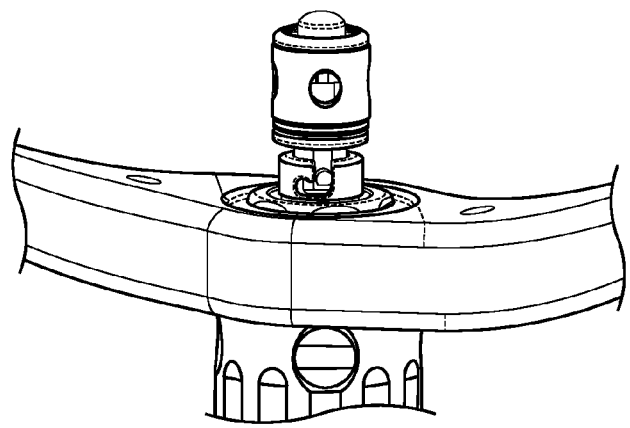
Figure 19R:
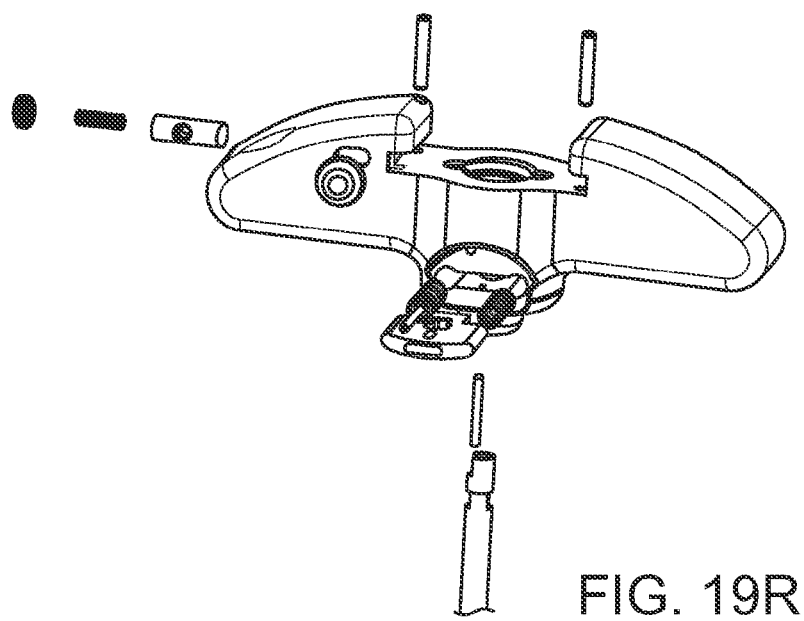
Figure 19S:
Figure 19T:
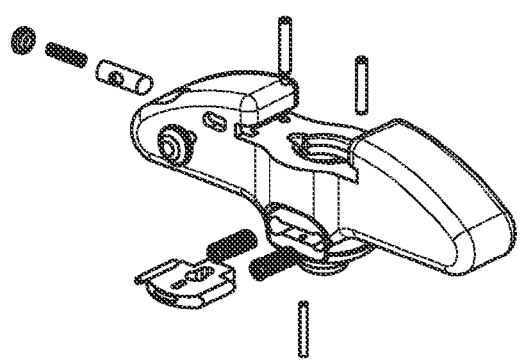
Figure 19U:
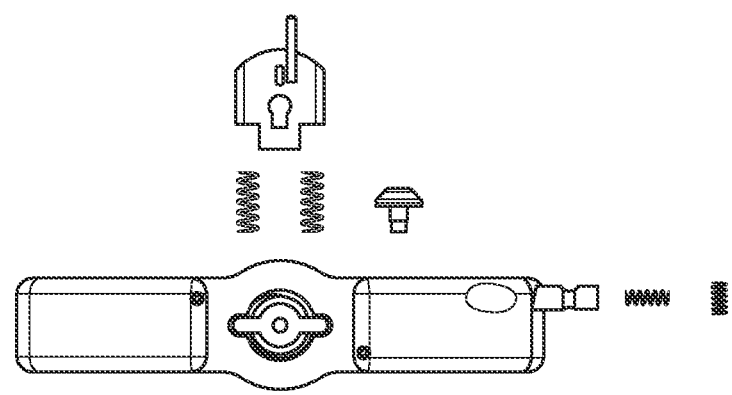
Figure 19V:
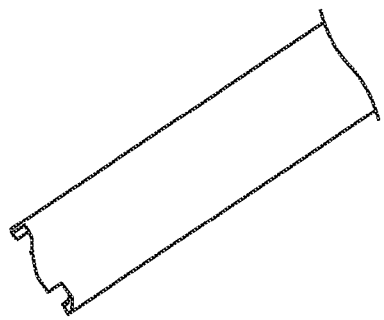
Figure 19W:
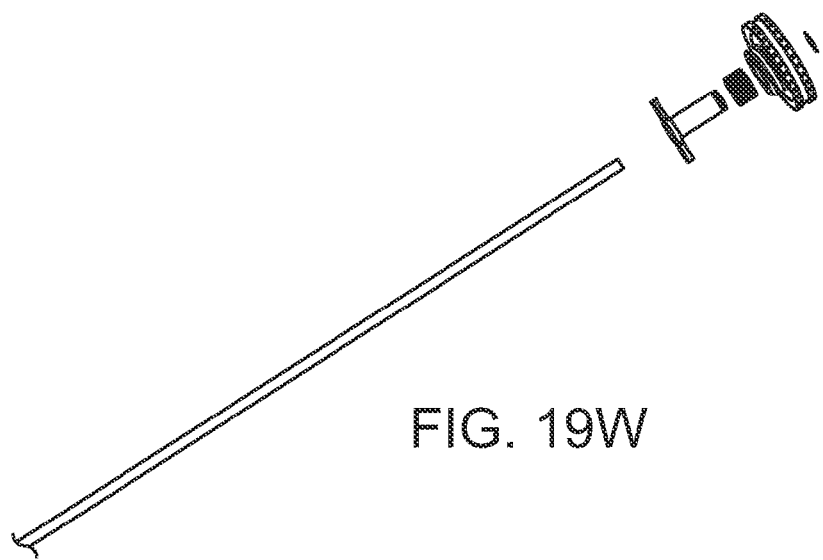

FIGS. 19A-19W show another embodiment of an Osseofix Fracture reduction system that includes 4 major components to deliver and deploy (expand) the Osseofix implant, the actuator, actuation rod, quick connect inerter handle and implant locking tube assembly.

The actuator generates the compressive force required to compress and expand the Osseofix Implants by converting the torque applied to the Actuator Handle to a linear compressive force through the use of a Power Screw located in the center of the Actuator. The actuator includes subcomponents housing, thrust nut, handle, power screw and thrust bearing.

The housing:
Cylindrical component that contains the Power Screw, Thrust Nut, Thrust Bearing in the proximal chamber of the housing.
Housing has rectangular cutout in the in the bottom of the proximal chamber to prevent the Power Screw from turning when the Power Screw is subjected to torque.
Two tabs at the bottom of the distal chamber allow the housing to couple with the Inserter Quick Connect Handle.
Distal chamber provides clearance from the Inserter Quick Connect Handle and gives space to allow the Power Screw to translate linearly.
Groove in the top of Housing holds a retaining ring to keep the Actuator components in place.

Thrust nut:
Connected to the Actuator Handle via a hex shaped section of the Nut.
Internally threaded to mate with the Power Screw.
Rotates within the housing when the Handle is turned to transmit a linear force to the Power Screw as the threads turn.
The Thrust Nut is supported by a roller thrust bearing within the Housing to reduce friction.

The handle:
Connected to the Thrust Nut via a hex cutout.
Transmits torque applied by hand from the surgeon to the Thrust Nut.
Handle shaped in an S pattern to help identify direction of torque that the surgeon needs to apply.

The power screw:
Directly interfaces with the Actuator Rod which transmits the compressive deployment force to the Implant.
Flats on distal end of power screw interact with the rectangular cutout in the housing to prevent rotation when loaded by the Thrust Nut.
Acme threads mate with the Thrust Nut to generate a linear force as the Thrust Nut is turned.
"J" shaped cutouts in the proximal end of the Power Screw mate with prongs of the Actuator Rod to create a bayonet type mount.
The "J" shaped cutouts are designed to prevent the Actuator Rod prongs from engaging the Power Screw unless the Actuator Rod is fully threaded into the Osseofix Implant.
A groove on the distal end of the Power Screw holds a retaining ring. This ring contacts the bottom of the proximal chamber in the Housing to provide a stop that sets a precise amount of travel for proper Implant deployment.

The thrust bearing:
Fits between the Thrust Nut and Housing to reduce friction when the Thrust Nut is turned.
Consists of thrust washers, roller bearings and a cage to maintain roller spacing.

The actuation rod includes subcomponents rod, knob and hub.

The Rod:
Threaded tip screws into distal end of implant.
Threaded tip is fluted to help dislodge bone that maybe trapped in the Implant threads.
Boss on proximal end of Rod interfaces with the Power Screw to transmit the compressive load to the distal end of the Implant. The distance between the end of the threads on the threaded tip and the proximal surface of boss is set to ensure that the proper distance.

The knob:
Prongs on the distal end of the Knob engage "J" slots in the proximal end of the Power Screw to positively lock the Actuator Rod to the Power Screw.
Internal cogs inside knob engage external cogs in the Actuator Hub to transmit torque and allow threading of the Rod into the distal threads of the Implant.
A spring inside the Knob keeps the cogs engaged during the threading process. After the Rod has been fully threaded into the Implant the Knob is pressed down to release the cogs and allow alignment of the prongs to the "J" slots in the Power Screw.
A groove in the top of the Knob holds a retaining ring to keep the spring in place.

The Hub:
The Hub is solidly attached to the rod.
External cogs engage a matching set of internal cogs to lock the Hub and Knob together during the threading of the Actuator Rod into the distal thread of the Implant.
The distal shape of the Hub acts to support and center the spring to allow free operation when the Knob is depressed to unlock the cogs after the threading into the Implant.

The quick connect inserter handle holds the disposable implant inserter shaft. a sliding lock with a keyhole shaped cutout engages twin notches in the implant inserter shaft, and undercuts in the proximal end of the handle engage the tabs of the actuator housing to provide a positive coupling. the actuator is kept coupled to the handle by means of a sliding spring loaded latch. The quick connect inserter handle includes subcomponents handle, sliding lock and latch.

The handle:

The Handle provides the primary means of stabilizing the system during Implant deployment.

The Handle is sized to allow the surgeon to provide a counter torque to the Actuator Handle during deployment of the Implant.

Undercuts in the top of the Handle provide a means of engaging the tabs of the Actuator Housing and positively coupling the Actuator and Handle together during deployment of the Implant.

A central bore through the Handle interfaces with the Implant Inserter Shaft. A cross pin the bore interfaces with a flat on the proximal end of Implant Inserter Shaft and aids in the alignment of the Inserter Shaft to the Sliding Lock.

The sliding lock:

The Sliding Lock fits into a side slot in the Handle. Springs in the bottom of the slot keep the Sliding Lock in the capture position with the narrow end of the keyhole cutout positioned over the central bore in the Handle.

When the Sliding Lock is depressed it disengages the Implant Inserter Shaft by centering the larger circular end of the keyhole cutout over the central bore of the handle.

The Sliding Lock is captured in the Handle by a pin that is pressed through an oblong slot in Sliding Lock.

The latch:

A spring loaded Latch acts to keep the Actuator Housing tabs contained within the undercuts in the Handle.

The Latch fits within a bore perpendicular to the cutouts and blocks the one of the openings through the undercuts.

The end of the Latch is shaped to allow the Actuator Tabs to depress the Latch when the Actuator turned to lock the Tabs in the undercuts.

A knob attached to the side of the Latch allows the Latch to be slid back into the bore to release the Actuator Housing Tabs.

The implant locking tube assembly slides down inside the implant inserter shaft and is held in place by a threaded knob that screws into the implant inserter quick connect handle. The saw teeth pattern cutouts in the distal end of the implant locking tube assembly engage slots in the proximal end of the implant to prevent unthreading of implant from the implant inserter shaft and the implant locking tube assembly is spring loaded to maintain positive contact with the proximal end of the implant. The implant locking tube assembly includes subcomponents locking tube, threaded knob and locking tube body.

The locking tube:

Slides down the Implant Inserter Shaft to engage the proximal end of the Implant.

Saw tooth pattern cutouts engage slots cut into the proximal end of the Implant.

The profile of the saw tooth pattern cutouts is orientated to allow the implant to be threaded into the Implant Inserter Shaft. The ramp of the tooth profile allows the tube to retract during threading of the Implant into the Implant Inserter Shaft. The vertical edge of the saw tooth pattern prevents the Implant from unthreading from the Implant Inserter Shaft.

The threaded knob:

Screws into the Implant Inserter Quick Connect Handle to secure the Locking Tube in place.

The perimeter of the Threaded Knob provides a boss to center and guide the bore of Actuator Housing distal chamber during the coupling of the Actuator to the Implant Inserter Quick Connect Handle.

A chamber in the Threaded Knob houses a spring that provides the locking force for the Locking Tube.

The locking tube body:

Is solidly attached to the Locking Tube.

T-shaped distal end of the Locking Tube Body engages a slot in the distal end of the Quick Connect Inserter Handle to prevent rotation of the Locking Tube.

A boss on the proximal end of the Locking Tube Body fits through a hole in the Threaded Knob and allows the Locking Tube to move axially as the tube engages the proximal end of the implant.

A groove on the proximal end of Locking Tube Body retains the spring that provides the locking force.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A surgical implant insertion system for deployment and removal of an expandable implant into a vertebral body, comprising:

an actuation rod including a distal end with threading that couples with a thread of a first distal end of the expandable implant;

an actuator handle coupled to a proximal end of the actuation rod;

an inserter locking tube disposed over the actuation rod and including a proximal end coupled to an inserter handle and including a distal end with threading that couples with a thread of a second proximal end of the expandable implant;

wherein upon insertion of the expandable implant into the vertebral body using the inserter handle, the actuator handle is turned causing the actuation rod to expand or compress the expandable implant coupled with the distal end of the inserter locking tube by applying force to the first distal end.

2. The system according to claim 1, further comprising a hydraulic assembly for hydraulically expanding and compressing the implant disposed at the distal end of the inserter locking tube.

3. The system according to claim 1, wherein the inserter handle includes a locking mechanism for interlocking the inserter locking tube.

4. The system according to claim 1, wherein the actuator handle includes a stopping mechanism configured to prevent turning of the actuator handle past a predetermined angle.

5. The system according to claim 1, wherein the inserter locking tube is configured to accommodate different size and shape implants.

6. The system according to claim 1, wherein the implant is a stent.

7. The system according to claim 1, further comprising a bone biopsy cannula configured to be inserted through the inserter locking tube.

8. The system according to claim 7, wherein the bone biopsy cannula can be configured to allow delivery of a bone cement.

9. The system according to claim 1, wherein upon insertion of the implant, the implant can be configured to a deployed/expanded state within the vertebral body by rotating the actuator handle in a clockwise direction.

10. The system according to claim 9, wherein upon insertion and configuration of the implant to the deployed/expanded state, the implant can be configured to an undeployed/unexpanded state to be repositioned by rotating the actuator handle in a counterclockwise direction.

11. A surgical implant insertion system for reducing spinal fractures of a vertebral body, comprising:
- an expandable implant including a proximal end and a distal end;
- an instrument for inserting and deploying the expandable implant including:
  - an actuation rod including a distal end that couples with the distal end of the expandable implant;
  - an actuator handle coupled to a proximal end of the actuation rod;
  - an inserter locking tube disposed over the actuation rod and including a proximal end coupled to an inserter handle and a distal end that couples with the proximal end of the expandable implant;
- wherein upon insertion of the expandable implant into the vertebral body using the inserter handle, the actuator handle is turned causing the actuation rod to apply a force on the distal end of the expandable implant,
- wherein the actuator rod applies a compressive force to expand the expandable implant to an expanded state for deployment within the vertebral body,
- wherein the actuator rod applies a tensile force to contract the expandable implant to an unexpanded state for repositioning within the vertebral body.

* * * * *